US008956379B2

(12) United States Patent  
Luciano et al.

(10) Patent No.: US 8,956,379 B2  
(45) Date of Patent: Feb. 17, 2015

(54) MEDICAL OSCILLATING COMPLIANCE DEVICES AND USES THEREOF

(75) Inventors: Mark G. Luciano, Highland Heights, OH (US); Stephen M. Dombrowski, University Heights, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 807 days.

(21) Appl. No.: 12/009,640

(22) Filed: Jan. 18, 2008

(65) Prior Publication Data

US 2009/0177279 A1 Jul. 9, 2009

Related U.S. Application Data

(63) Continuation of application No. PCT/US2006/028354, filed on Jul. 21, 2006.

(60) Provisional application No. 60/701,596, filed on Jul. 21, 2005, provisional application No. 60/735,388, filed on Nov. 10, 2005.

(51) Int. Cl.
*A61M 29/00* (2006.01)
*A61M 27/00* (2006.01)
(Continued)

(52) U.S. Cl.
CPC ........... *A61M 27/006* (2013.01); *A61M 1/1072* (2013.01); *A61M 25/1018* (2013.01); *A61M 25/10* (2013.01)
USPC ................... 606/192; 91/28; 91/210; 604/65; 604/93.01; 604/96.01; 604/97.01; 604/503; 604/891.1

(58) Field of Classification Search
USPC ........... 606/192; 91/28, 39, 210, 281; 604/65, 604/93.01, 96.01, 97.01, 503, 891.1
See application file for complete search history.

(56) References Cited

U.S. PATENT DOCUMENTS

| 4,519,403 A | 5/1985 | Dickhudt |
| 4,686,085 A | 8/1987 | Osterholm |

(Continued)

FOREIGN PATENT DOCUMENTS

| DE | 299 21 166 U1 | 4/2000 |
| EP | 0 808 184 B1 | 10/1998 |

(Continued)

OTHER PUBLICATIONS

Dombrowski, S.M., et al., "Chronic Hydrocephalus-Induced Changes in Cerebral Blood Flow: Mediation Through Cardiac Effects," *J. Cereb Blood Flow Metab.*, 26:1298-1310 (Feb. 22, 2006).

(Continued)

*Primary Examiner* — Victor Nguyen
*Assistant Examiner* — Kevin Everage
(74) *Attorney, Agent, or Firm* — Hamilton, Brook, Smith & Reynolds, P.C.

(57) ABSTRACT

The present invention relates to devices and systems that alter intracranial compliance, cerebral blood flow and/or intracranial pressure pulsatility/waveform by oscillating the contraction and expansion of a compressible composition within the cranial or spinal cavities such that they increase intracranial capacity. The contraction and expansion of the compressible composition in the oscillating compliance devices can be due to an individual's intracranial pressure, the result of the expansion and compression of a reservoir which is mediated by the contractility of the heart or driven by a pump gaited to a biorhythm. The invention also relates to methods for protecting an individual's brain from abnormal arterial pulsations and for altering an individual's cerebral blood flow using the devices and systems of the invention. The oscillating compliance devices can be used to treat several diseases and/or conditions characterized by altered/abnormal intracranial compliance, cerebral blood flow and/or intracranial pressure pulsatility/waveform, including hydrocephalus, stroke, dementia and migraine headaches, vasospasms, congestive heart failure, cardiopulmonary bypass or carotid endarterectomy.

24 Claims, 28 Drawing Sheets

(51) Int. Cl.
*A61M 1/10* (2006.01)
*A61M 25/10* (2013.01)

(56) References Cited

U.S. PATENT DOCUMENTS

| | | | |
|---|---|---|---|
| 4,767,400 A | | 8/1988 | Miller et al. |
| 5,084,016 A | | 1/1992 | Freeman et al. |
| 5,693,989 A | * | 12/1997 | Satomi et al. ............. 310/12.17 |
| 5,711,507 A | * | 1/1998 | Berget et al. ............. 251/129.04 |
| 5,957,912 A | | 9/1999 | Heitzmann |
| 5,980,480 A | * | 11/1999 | Rubenstein et al. ............. 604/9 |
| 6,105,582 A | | 8/2000 | Pranevicius |
| 6,683,066 B2 | | 1/2004 | Wang |
| 2003/0167031 A1 | | 9/2003 | Odland |
| 2003/0236442 A1 | * | 12/2003 | Connors et al. ............. 600/29 |
| 2005/0187430 A1 | | 8/2005 | Aundal et al. |

FOREIGN PATENT DOCUMENTS

| | | |
|---|---|---|
| EP | 1 676 527 A1 | 7/2006 |
| WO | WO 98/02202 | 1/1998 |
| WO | WO 99/07276 | 2/1999 |
| WO | WO 01/39819 A2 | 6/2001 |
| WO | WO 2009/058353 | 5/2009 |

OTHER PUBLICATIONS

Egnor, M. et al., "A Model of Intracranial Pulsations," *Pediatr. Neurosurg.*, 35(6):284-298 (Dec. 2001).

Egnor, M. et al., "A Model of Pulsations in Communicating Hydrocephalus," *Pediatr. Neurosurg.*, 36(36):281-303 (Jun. 2002).

Egnor, M. et al., "Resonance and the Synchrony of Arterial and CSF Pulsations", *Pediatr. Neurosurg.*, 38:273-276 (2003).

Fukuhara, T., et al., "Effects of Ventriculoperitoneal Shunt Removal on Cerebral Oxygenation and Brain Compliance in Chronic Obstructive Hydrocephalus," *J Neurosurg,*. 94(4):573-581 (Apr. 2001).

Greitz, D., "Radiological Assessment of Hydrocephalus: New Theories and Implications for Therapy", *Neurosurg. Rev.*, 27:145-165 (May 26, 2004).

Greitz, D., "The Hydrodynamic Hypothesis Versus the Bulk Flow Hypothesis," *Neurosurg. Rev.*, 27:299-300 (Jul. 23, 2004).

Heymann, M.A., et al., "Blood Flow Measurements With Radionuclide-Labeled Particles", *Prog. Cardiovasc. Dis.*, 20(1):55-79 (Jul.-Aug. 1977).

Johnson, M.J., et al., "Development and Characterization of an Adult Model of Obstructive Hydrocephalus," *J. Neurosci Methods*, 91:55-65, (1999).

Luciano, M.G., et al., "Cerebrovascular Adaptation in Chronic Hydrocephalus," *J. Cereb. Blood Flow Metab.*, 21(3):285-294 (2001).

Nov. 28, 2006, Notification of Transmittal of the International Search Report and the Written Opinion of the International Searching Authority, or the Declaration, PCT/US2006/028354.

Feb. 20, 2007, Amendment Under Article 34 and Reply to First Written Opinion, PCT/US2006/028354.

Jul. 6, 2007, Supplemental Amendment Under Article 34 and Reply to Written Opinion, PCT/US2006/028354.

Jul. 30, 2007, Notification of Transmittal of the International Preliminary Report on Patentability, PCT/US2006/028354.

Feb. 10, 2009, Notification of Transmittal of the International Search Report and the Written Opinion of the International Searching Authority, or the Declaration, PCT/2008/012355.

* cited by examiner

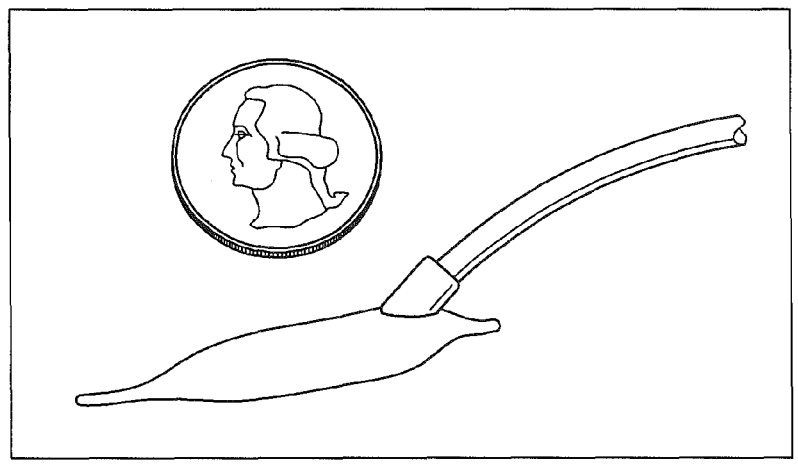
FIG. 10
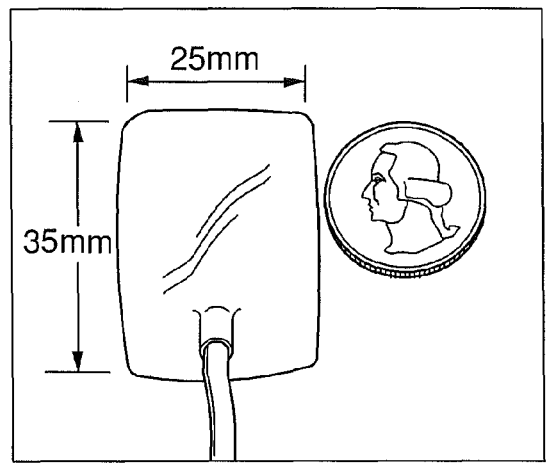
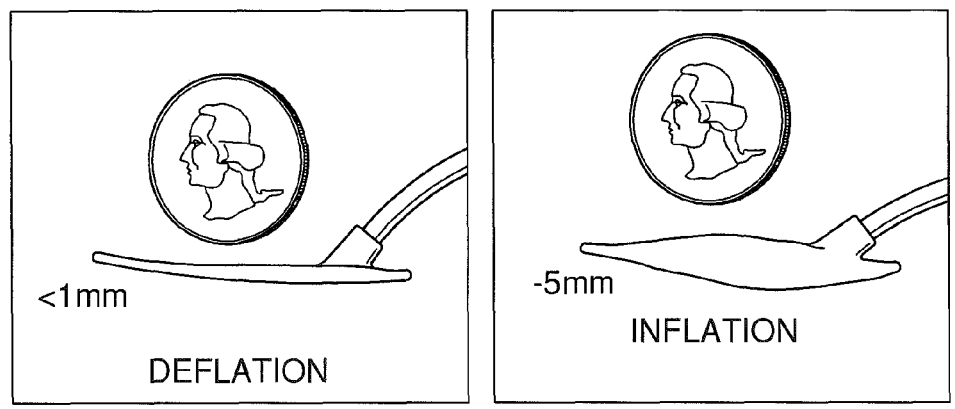
FIG. 11

FIG. 22A
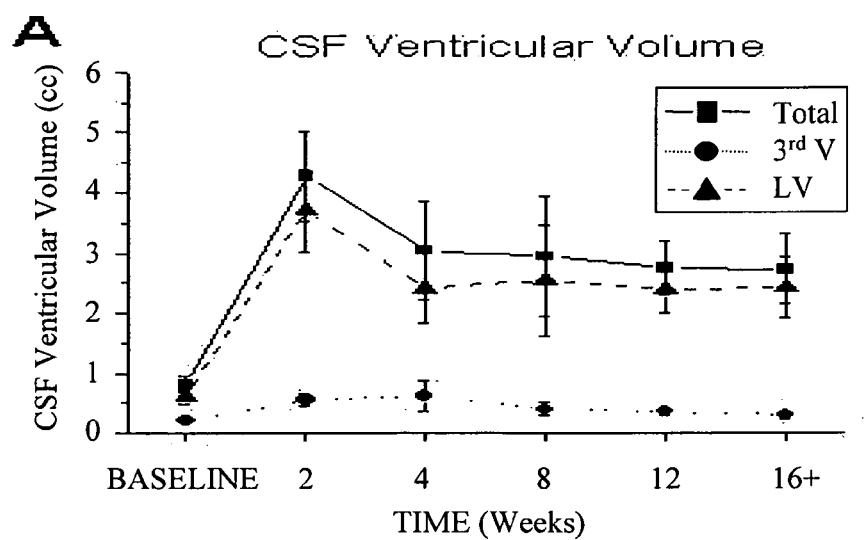
FIG. 22B
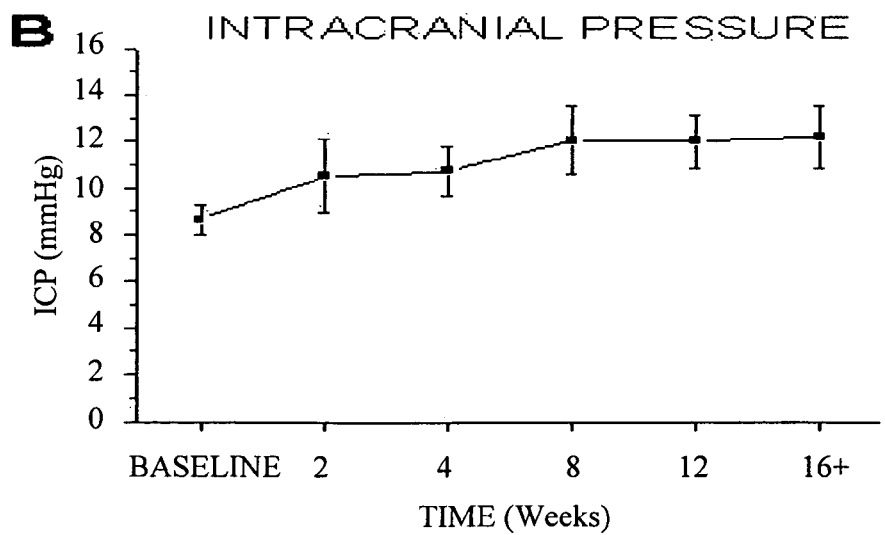
FIGs. 22A-22B

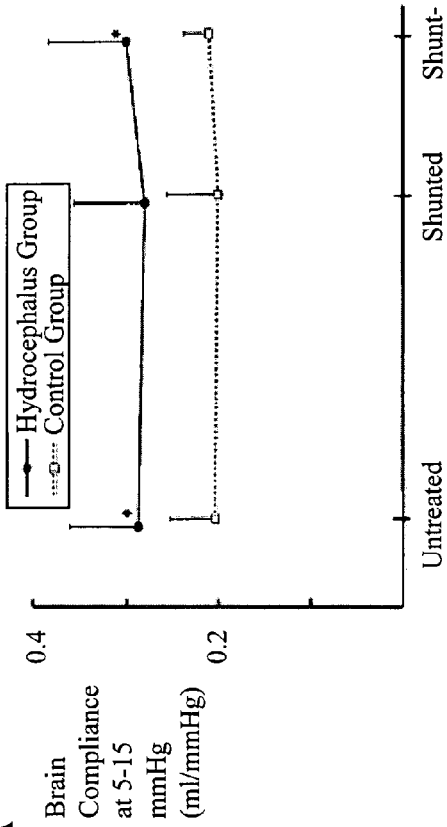
FIG. 24A
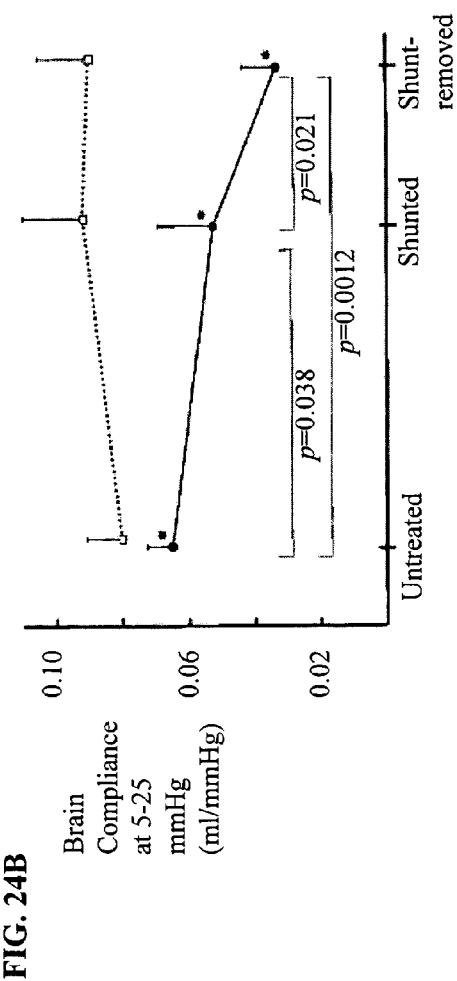
FIG. 24B
FIGs. 24A-24B

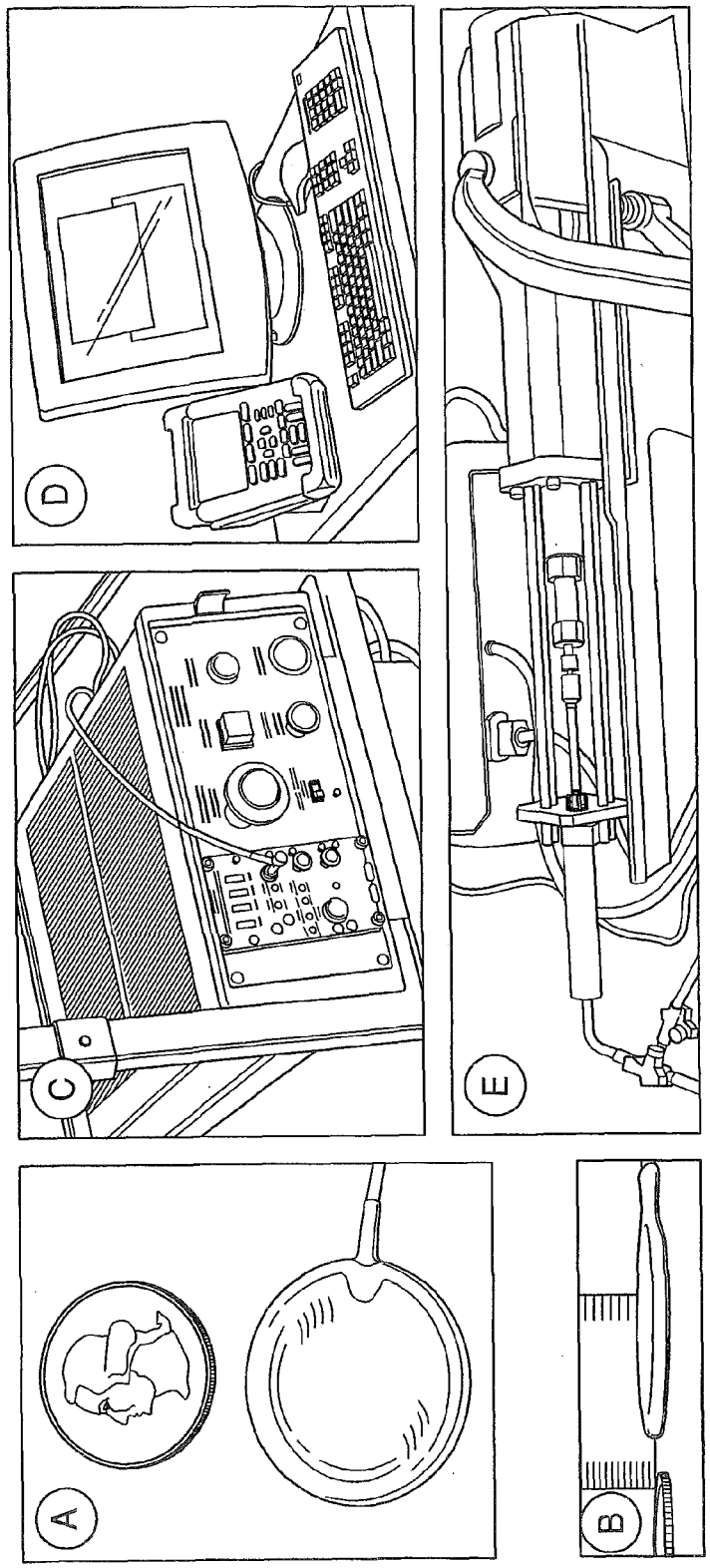

FIGs. 27A-27E

Photograph of an embodiment of the cranial-epidural OCD. The internal balloon catheter (A, B) (approximately 25mm diameter,1mm thickness) can be used for a range of 0.1-5.0cc of a fluid gas. The OCD pump system is made up of ECG cardio-tachometer, R-wave discriminator, digital display (C), inflation-deflation interface software program (D), and computer controlled reciprocating pump, stepper motor and 24mm diameter/50mmstroke anti-stiction air cylinder (E).

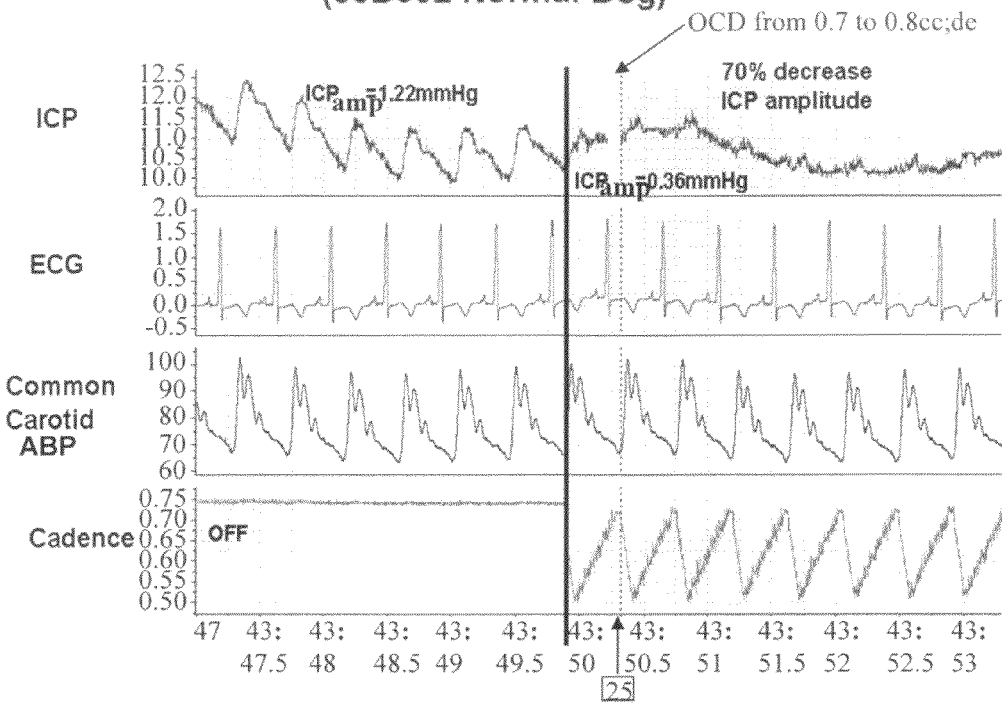
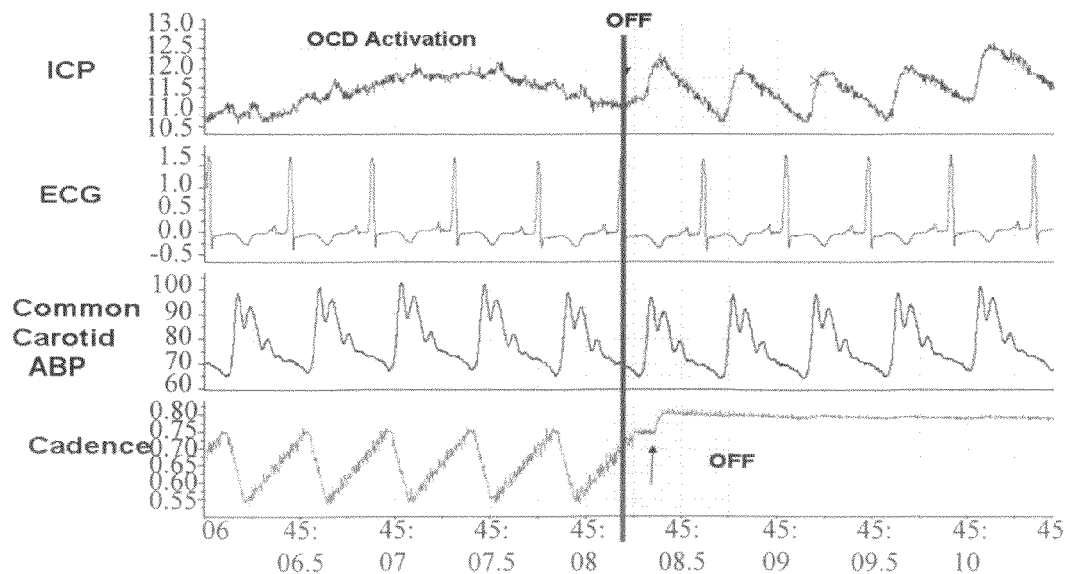
FIG. 28

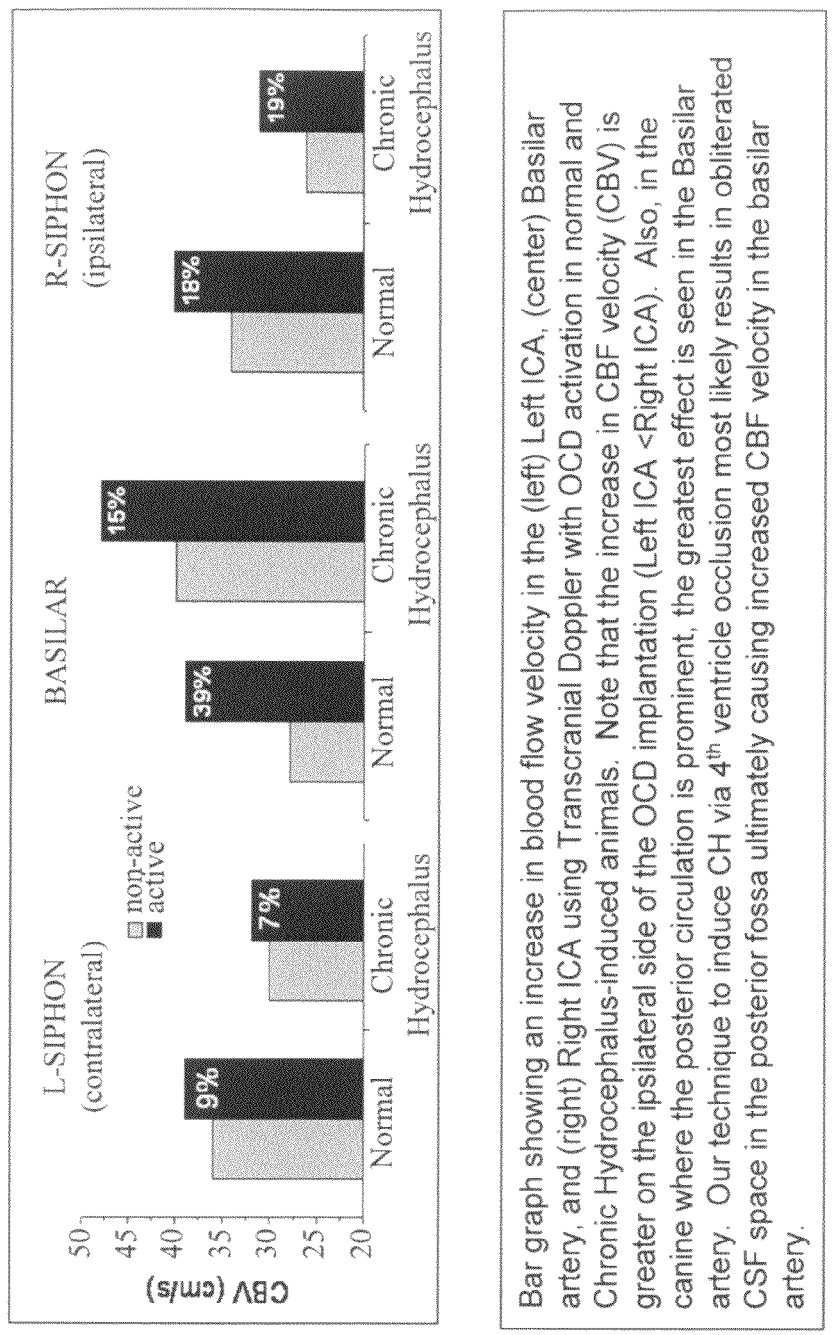

FIG. 29

Bar graph showing an increase in blood flow velocity in the (left) Left ICA, (center) Basilar artery, and (right) Right ICA using Transcranial Doppler with OCD activation in normal and Chronic Hydrocephalus-induced animals. Note that the increase in CBF velocity (CBV) is greater on the ipsilateral side of the OCD implantation (Left ICA <Right ICA). Also, in the canine where the posterior circulation is prominent, the greatest effect is seen in the Basilar artery. Our technique to induce CH via 4th ventricle occlusion most likely results in obliterated CSF space in the posterior fossa ultimately causing increased CBF velocity in the basilar artery.

MEDICAL OSCILLATING COMPLIANCE DEVICES AND USES THEREOF

RELATED APPLICATIONS

This application is a Continuation of International Application No. PCT/US2006/028354, filed on Jul. 21, 2006, which claims the benefit of U.S. Provisional Application No. 60/701,596, filed Jul. 21, 2005, and U.S. Provisional Application No. 60/735,388, filed Nov. 10, 2005, the contents of which are incorporated herein by reference in their entirety.

BACKGROUND OF THE INVENTION

Decreased cerebral blood flow (CBF) is a significant problem seen in the most common and devastating brain disorders, including chronic hydrocephalus, stroke and dementia. Increasing clinical and experimental evidence indicate that the underlying cause in these and other neurological disorders symptomatic of decreased CBF stems from a loss of intracranial compliance (ICC).

In order for blood to enter the closed space of the rigid cranium, the brain must give way or be "compliant." This idea is key to intracranial dynamics which involve the conduction of arterial blood pulse waves from the extracerebral arteries, via the cerebral spinal fluid (CSF), to the veins and spinal cavity, allowing the pulse waves to bypass the brain and its capillaries. Normally, arteries, when compliant, act as an elastic reservoir, the arterial walls absorbing part of the hydraulic energy in the pulse wave during systole. This energy is then released during diastole in order to maintain constant capillary flow. Termed the "Windkessel effect," this process changes the pulse of arterial blood flow into a nearly continuous, non-pulsating capillary flow, decreasing the speed and force at which arterial pulse pressure is transmitted to the capillaries and the brain tissue in order to protect them from these forces.

However, in many brain disorders, intracranial hydrodynamics have become abnormal. Events that restrict arterial pulsations may cause these intracranial hydrodynamic abnormalities resulting in a decrease in intracranial compliance. For example, trauma and insults to and adhesions in the subarachnoid space can restrict arterial pulsations, causing a decrease in intracranial compliance. Similarly, any vascular disorder that results in increased capillary pulse pressure can lead to decreased ICC.

In brain disorders involving decreased intracranial compliance, arterial blood pulsations that reach the brain are poorly dampened or buffered, if at all. This breakdown in buffering by the Windkessel effect results in increased intracranial pulse pressure or pulsatility that acts directly on the brain, injuring the capillaries and brain tissue. In addition, decreased intracranial compliance causes increased vascular impedance, increased vascular resistance to convective blood flow (due to compressed arteries and veins) and, consequently, reduced cerebrovascular blood flow efficiency. In fact, these insults to the brain can account for the edema, brain thinning, decreased CBF and decreased brain function seen in vascular dementia, hydrocephalus, stroke and other neurologic diseases.

Traditionally, it has been believed that in brain disorders such as hydrocephalus, which is characterized by an increased volume of CSF in the brain, the pathology of the disease was due to an imbalance between CSF formation in the choriod plexus and CSF absorption in the capillaries of the central nervous system. Thus, one approach to treat hydrocephalus involved the draining or shunting of excess fluid from the CSF compartment to the subarachnoid space. However, shunting has not been effective in treating a number of patients and some now believe that the pathology of the disease may be due to a decrease in intracranial compliance, a problem shunting can not adequately address. Further, shunting is invasive, having the potential to damage and/or cause infection in the brain, is problematic in that the CSF is drained at non-physiological levels and is not a permanent solutions to hydrocephalus. Similarly, the treatments for other brain disorders like stroke or dementia do not address the reduced ICC seen in the diseases, which may, in fact, be the root cause of those diseases.

Moreover, there are numerous non-neurological diseases or conditions in which it would be advantageous to alter (e.g., increase or decrease) ICC, cerebral blood flow (CBF) or intracranial pressure (ICP) pulsatility/waveform. For example, conditions like vasospasms are characterized by abnormally high ICP pulsatility, while individuals who experience and/or have experienced congestive heart failure, caroitid endarterectomy or a cardiopulmonary bypass procedure are known to have undesirably low ICP pulsatility (see FIG. 1).

All of these diseases/conditions could benefit from a treatment that alters abnormal and/or undesirable ICC, CBF and ICP pulsatility/waveform. Thus, what is needed is a device that restores ICC by restoring the proper buffering of arterial pulsations in the brain, alters the flow of blood to the brain such that it is appropriate and/or modulates the ICP waveform such that the pulsatility is in a normal range.

SUMMARY OF THE INVENTION

The present invention relates to devices and systems that alter intracranial compliance (ICC), cerebral blood flow (CBF), intracranial pressure (ICP) pulsatility/waveform or combination thereof in an individual. In a particular embodiment, the devices and systems of the present invention can be used to restore ICC, CBF and/or ICP pulsatility/waveform in an individual. The device works by oscillating contraction and expansion of a compressible composition in order to alter (increase or decrease) ICC, CBF and/or ICP pulsatility/waveforms. In one embodiment the device is an "oscillating compliance device" (OCD), also referred to herein as a "cadence", comprising a compressible composition that is capable of free expansion and compression to affect an individual's ICC, CBF and/or ICP pulsatility. In a further embodiment, the compressible composition is a balloon catheter filled with a substance like a fluid, gas or malleable substance (e.g., a hydrogel). In another embodiment, the oscillating compliance device further comprises an external reservoir coupled to the compressible composition which is capable of being placed extra-craniospinally, subcutaneously or within a body cavity. In yet another embodiment, the oscillating compliance device is also comprised of an intracranial monitor, blood flow probe or oxygen probe to measure ICP or CBF within the patient's cranial space. The oscillating compliance device is capable of being placed within an epidural or CSF space of either the patient's brain or spinal cord.

In another embodiment, the oscillating compliance device is comprised of a compressible composition, a pump coupled to the compressible composition that provides for the expansion and compression of the compressible composition, an external reservoir coupled to the pump and a biorhythm sync connected to the pump for connecting to a source of a patient's biorhythm in order to synchronize the pump with the patient's biorhythm. In one embodiment, the compressible composition is a balloon catheter comprising a substance like a fluid, gas or malleable substance. In another embodiment, the external reservoir can be placed in an extra-craniospinal or subcutaneous space or within a body cavity. In yet another embodiment, the biorhythm sync is a cardiac sync and further, the biorhythm source is the electrical rhythm/signal of the patient's heart. In another embodiment, the pump is powered by either a motor-powered battery or a physiologically-derived source. In this embodiment, the oscillating compliance device is also capable of being placed within the epidural or CSF space of the patient's brain or spinal cord. In another embodiment, the oscillating compliance device is also comprised of one or more monitoring devices like an intracranial monitor for measuring the patient's ICP waveform, a blood flow probe and/or an oxygen probe and can further comprise a control system in communication with the pump that automatically adjusts the pump's expansion and compression of the compressible composition based on the measurements of these one or more monitoring devices.

In another embodiment, the present invention relates to an oscillating compliance device comprised of a compressible composition, a tube coupled to the compressible composition and an external reservoir that is placed in a patient's pericardial space and coupled to the tube, such that the external reservoir is capable of free expansion and compression due to the contraction and expansion of the patient's heart. The tube connects the compressible composition to the external reservoir allowing free exchange between the two. In one embodiment, the compressible composition is a balloon catheter comprising a fluid, gas or a malleable substance. In another embodiment, the compressible composition is capable of being placed within an epidural or CSF space of the patient's brain or spinal cord.

The invention also relates to oscillating compliance systems. In one embodiment, the oscillating compliance system comprises one or more oscillating compliance devices having a compressible composition capable of free expansion and compression to affect an individual's ICC, CBF and/or ICP pulsatility. In another embodiment, the oscillating compliance system comprises one or more oscillating compliance devices having a compressible composition, a pump coupled to the compressible composition for expansion and compression of the compressible composition, an external reservoir coupled to the pump and a biorhythm sync for connecting to a source of a patient's biorhythm in order synchronize the pump with the patient's biorhythm. In both oscillating compliance systems, the compressible composition of the one or more oscillating compliance devices can be a balloon catheter comprising a substance like a fluid, gas or malleable substance. The oscillating compliance devices are capable of being placed within an epidural or CSF space of the patient's brain or spinal cord. In yet another embodiment, the oscillating compliance systems can be further comprised of an intracranial monitor, blood flow probe or oxygen probe to measure ICP or CBF within the patient's cranial space.

The present invention also relates to a method for protecting an individual's brain from arterial pulsations entering the individual's cranial cavity comprising displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression. In one embodiment, the compressible composition of the one or more oscillating compliance devices is located in the internal space and is a balloon catheter comprising a substance like a fluid, gas or malleable substance. In yet another embodiment, the compressible composition of the one or more oscillating compliance devices is capable of being placed within an epidural or CSF space of the individual's brain or spinal cord. In another embodiment, the one or more oscillating compliance devices can comprise an external reservoir placed in the external space and can be located extra craniospinally, subcutaneously or within the body cavity.

The invention also relates to a method of increasing intracranial compliance in an individual by displacing a compressible substance from the individual's internal space to an external space during systole using one or more oscillating compliance devices having a compressible composition and returning the substance from the external space to the individual's internal space during diastole using the one or more oscillating compliance devices having a compressible composition.

The invention further relates to a method of controlling the size of an individual's CSF space in synchrony with incoming arterial pulsations comprising displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression.

The invention also relates to a method of increasing the volume capacity of an individual's thecal sac to facilitate the entry of arterial blood into the individual's cranial cavity comprising displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression.

The present invention also relates to a method of altering arterial blood pulsations in an individual's brain comprising displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression.

The invention further relates to a method of increasing the efficiency of an individual's cerebral blood flow and cerebrovascular circulation by modulating the individual's intracranial space comprising displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression.

The present invention also relates to a method of treating an individual (e.g., patient) having an altered ICC, CBF and/or ICP pulsatility comprising implanting an oscillating compliance device or an oscillating compliance system in the individual. In one embodiment, the patient is treated for diseases/conditions in which cerebral blood flow is altered (e.g., diminished, enhanced) such as vasospasms, congestive heart failure or carotid endarterectomy (e.g., carotid occlusion/ stenosis). In another embodiment, the OCD is implanted in a patient undergoing a cardiopulmonary bypass procedure. In this embodiment, one or more OCDs are implanted into the patient either before, during and/or after the cardiopulmonary bypass procedure, as needed. In yet another embodiment, the patient is treated for a hydrodynamic brain disorder that includes hydrocephalus, stroke, dementia or migraine headaches. In a further embodiment of the method, the hydrocephalus treated can be chronic hydrocephalus, normal pressure hydrocephalus, pseudotumor cerebri or slit ventricle syndrome. In another embodiment, the stroke treated can be acute stroke, chronic stroke, microvascular disease, dementia, Moya-Moya, multiple infarct disease, posterior circulation insufficiencies or Binswanger disease. In yet another embodiment, the dementia treated can be vascular dementia, Alzheimer's disease and normal pressure hydrocephalus. In another embodiment, the migraine headaches treated are pediatric migraines, adult migraines or intractable migraines.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 10 is a picture of an embodiment of an oscillating compliance device.

FIG. 11 is a picture of an embodiment of an oscillating compliance device, deflated and inflated.

FIG. 22A is a graph illustrating the changes in CSF ventricular volume over time in the experimental model of chronic obstructive hydrocephalus.

FIG. 22B is a graph illustrating the changes in ICP over time in the experimental model of chronic obstructive hydrocephalus.

FIGS. 24A-24B are graphs illustrating the changes in ICC at FIG. 24(A) normal ICP (5-15 mmHg) and FIG. 24(B) high ICP (15-25 mmHg) in animals having induced chronic hydrocephalus compared to control animals before and after CSF shunt treatment.

FIGS. 27A-27B are pictures of a prototype of an cranial-epidural oscillating compliance device comprising a balloon catheter.

FIG. 27C is a picture of an ECG cardio-tachometer, R-wave discriminator, and digital delay of a OCD system.

FIG. 27D is a picture of a computer running inflation-deflation interface software program of the OCD system.

FIG. 27E is a picture of the computer-controlled reciprocating pump, stepper motor and anti-stiction air cylinder of the OCD system.

FIG. 28 are graphs illustrating intraoperative data collection for ICP, ECG and ABP using the OCD system.

FIG. 29 is a graph illustrating the increase in blood flow velocity in the left ICA, Basilar artery and Right ICA using a transcranial doppler with an OCD device in animals with chronic hydrocephalus.

DETAILED DESCRIPTION OF THE INVENTION

Figure 1:
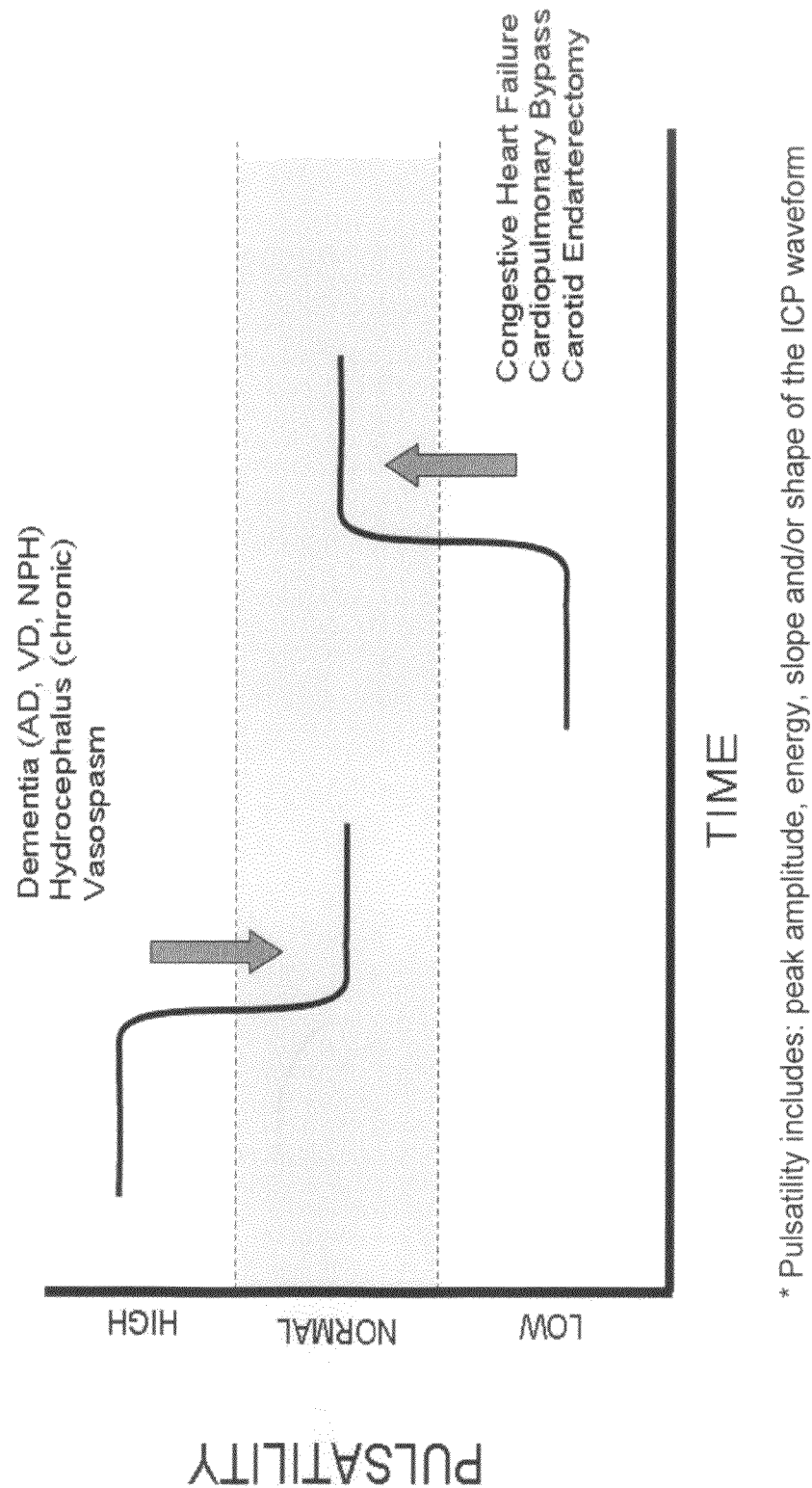
FIG. 1 is a schematic illustrating abnormal pulsatility in various disorders.
Figure 2:
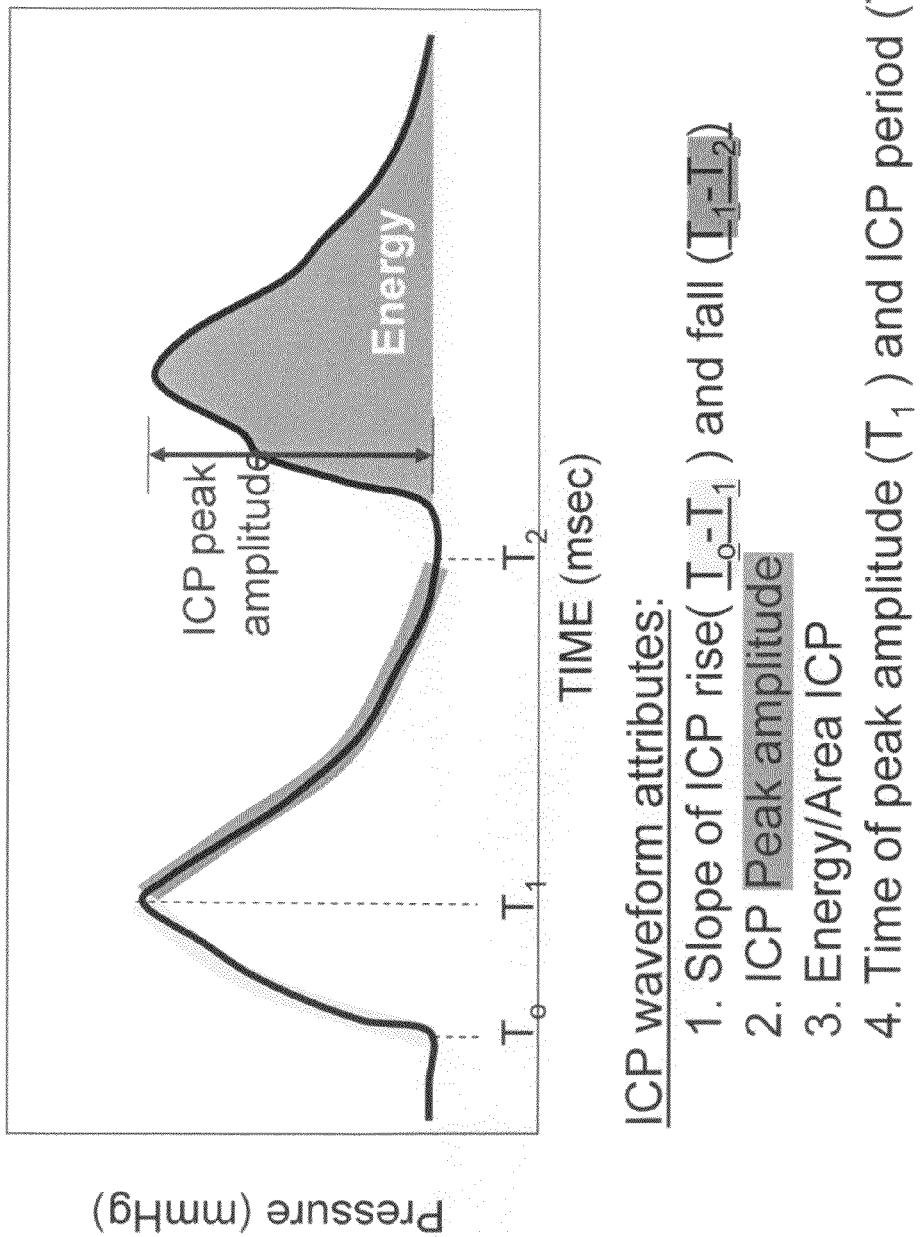
FIG. 2 is a schematic illustrating ICP waveform characteristics that can be altered by an OCD.

The present invention generally relates to a device that alters or modulates (e.g., increases, decreases) intracranial compliance (ICC) in an individual, cerebral blood flow (CBF), intracranial pressure (ICP) pulsatility/waveform or a combination thereof. In a particular embodiment, the device can restore ICC such that abnormal transmissions of arterial pulsations to the individual's brain capillaries and tissue are reduced and/or completely eliminated, CBF is altered such that it is in the desired and/or normal range and ICP pulsatility (e.g., peak amplitude, energy, slope and/or shape) is modulated as necessary (see FIGS. 1 and 2). This is accomplished by making small, controlled changes in the size of an individual's intracranial space which increase the volume capacity of the space in synchrony with incoming arterial blood flow pulsations. Modulating the size of the intracranial space with the incoming blood flow results in increased cerebrovascular circulation and, consequently, increased efficiency of the individual's cerebral blood flow. The device can be used to treat a patient suffering from any one of a number of conditions including, for example, hydrocephalus, stroke, dementia and migraine headaches, vasospasms congestive heart failure, carotid endarterectomy and before, during or after a cardiopulmonary bypass procedure.

Accordingly, the present invention relates to an "oscillating compliance device" (OCD) or "cadence" that provides for altered ICC, CBF or ICP pulsatility in an individual. In doing so, the oscillating compliance device addresses these disorders with minimal invasion of the brain. The device can be used in both acute and chronic situations to treat problems characterized by altered (e.g., increased or decreased) ICC, CBF or ICP pulsatility for those in need thereof.

Figure 3:
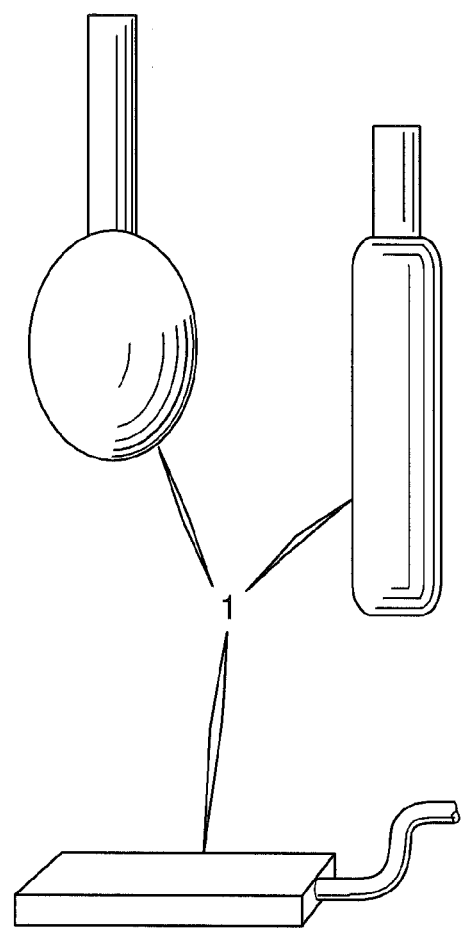
FIG. 3 is an illustration of various shapes and sizes of the compressible composition of the oscillating compliance device.

In one embodiment, the oscillating compliance device is comprised of a compressible composition that can expand and compress freely to affect an individual's ICC, CBF and/or ICP pulsatility, passively modulating intracranial capacity (a passive oscillating compliance device). This expansion and compression can be due to, for example, an individual's ICP. Any compressible composition that can repeatedly and/or reproducibly change volume (i.e., expand and deflate) in an enclosed space appropriate for use in a mammal can be employed, such as a balloon catheter, flat bladder or spherical system. In a particular embodiment, the compressible composition is a balloon catheter. The balloon catheter can be any known to those of skill in the art, and are commercially available (e.g., Datascope Corp. #0686-DM-0116-01). As shown in FIG. 3, compressible composition 1 can be of various shapes and sizes and can be appropriately modified for use in the device by the skilled artisan. The compressible composition can have a volume capacity from about 0.5 to about 2.0 cubic centimeters (cc). In particular embodiments, the compressible composition can have a volume capacity of about 0.75 to about 1.75 cc or of about 1 to about 1.5 cc.

The compressible composition can comprise a substance capable of being moved (i.e., transferred or transported) into and out of the cranial vault by a force such as intracranial pressure or a biological pulse (i.e., arterial or cardiac pulse pressure). The substance can be a fluid (e.g., a liquid), gas (e.g., helium, oxygen, carbon dioxide, air or a combination of gases) or a malleable substance. The malleable substance can include one of several hydrogels, or a deformable solid or semi-solid (e.g., mercury or a polymer), many of which are commercially available. In a particular embodiment, the substance is not in a completely solid state (e.g., the substance is a liquid or semi-solid). The volume of the substance necessary for use in the oscillating compliance device will vary according to the compressible substance chosen and is easily determined by one with skill in the art based on the properties of the substance, the placement of the oscillating compliance device in the individual and the dimensions of the compressible composition required for adequate treatment of the patient.

In a further embodiment, the compressible composition is not a closed system (e.g., balloon catheter, flat bladder or spherical system). Instead the compressible composition is an open system (e.g., an open catheter) that diverts the movable substance, in particular, a liquid like CSF or blood, out of the CSF or spinal space.

The oscillating compliance device can further comprise a reservoir which is coupled to the compressible composition. In one embodiment, the reservoir is external to the patient (i.e., is located outside the patient's body). In a particular embodiment, the reservoir is external to the patient's cranium. The reservoir can be used, for example, to provide a space into which the substance (e.g., a fluid, gas or malleable substance) can be displaced when the compressible composition (e.g., a balloon catheter) is under compression (e.g., due to the individual's ICP). Like the compressible composition, the reservoir can be made of any material (e.g., plastic or silicone) with an ability to expand and deflate (e.g., in an elastic manner) and can be placed in a variety of locations such as an extra-cranio or spinal space, a subcutaneous space in the head or body or in a body cavity, like the pericardial or peritoneal sac. In a particular embodiment, the reservoir is placed in a subcutaneous space, and is coupled to the compressible composition.

In another embodiment, the device comprises one or more monitoring devices which can include an intracranial monitor to measure the patient's ICP. Several ICP monitors are available commercially (e.g., from Spiegelberg or Codman & Shurtleff, Inc.), any of which can be used as part of the device. Many types of ICP monitors are available including intraventricular catheters, fibreoptic monitors, subarachnoid bolts, epidural monitors and transcranial dopplers. In a further embodiment, the one or more monitoring devices can also include a blood flow probe(s) to measure CBF and/or an oxygen probe(s) to measure the level of oxygen delivered to the brain by the blood. These probes are well-known in the art and also commercially available (e.g., Transonic Systems, Inc., Volcano ComboWire XT, Integra LICOX system). The type of monitors (intracranial, blood flow, oxygen) chosen for use in the device is dependent on several factors, including the disease being treated, and is best determined by one with skill in the art based on the particular patient's needs. As the oscillating compliance device is designed to alter intracranial waveform pulse pressure and CBF, these monitoring and measurement devices allow the skilled clinician to collect pertinent information and optimize the performance of the oscillating compliance device.

Figure 4:
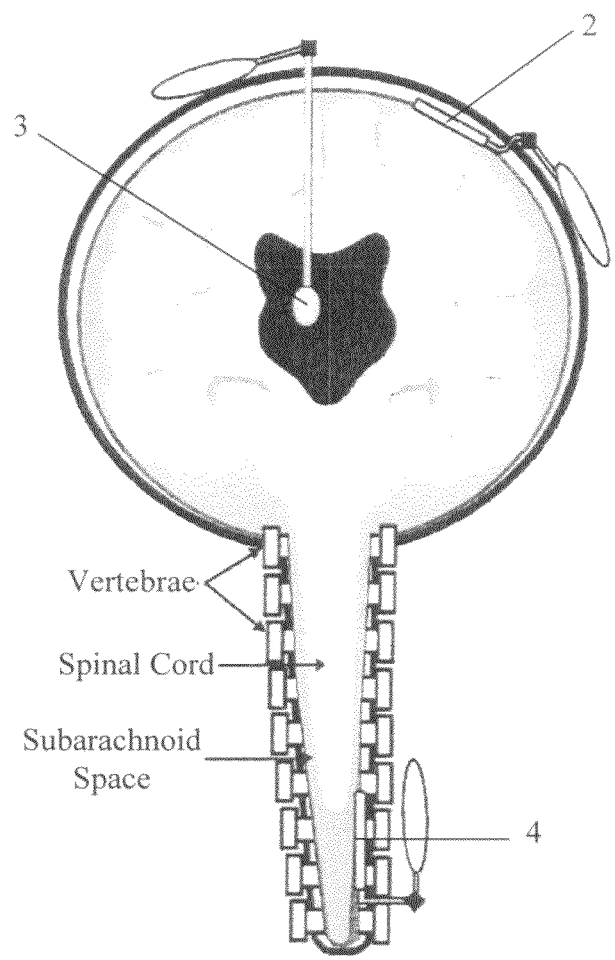
FIG. 4 is a schematic illustrating an embodiment of the oscillating compliance device and placement of the device in various locations including an epidural and CSF space of the brain and an epidural space of the spinal cord.
Figure 5:
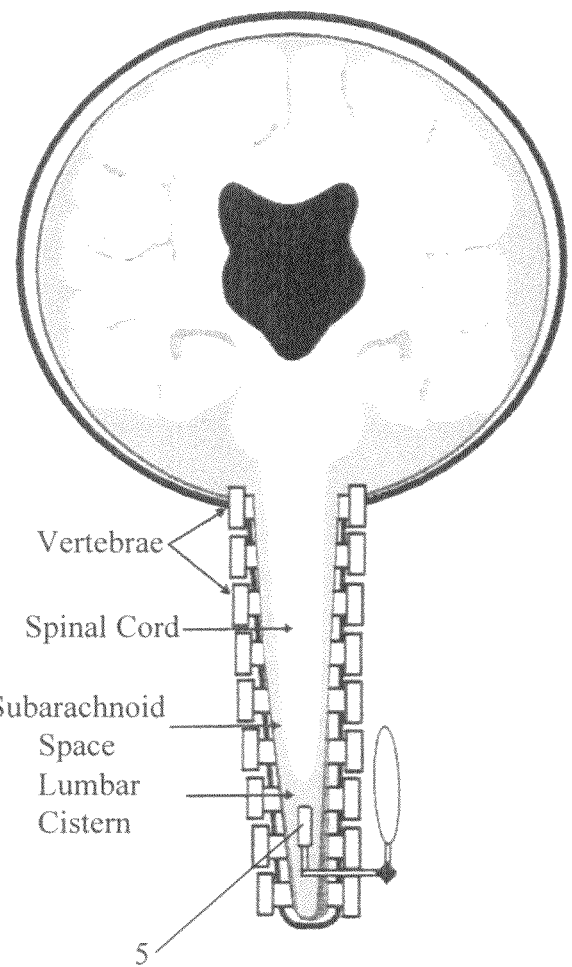
FIG. 5 is a schematic illustrating the placement of an embodiment of the oscillating compliance device in the CSF space of the spinal cord.
Figure 6:
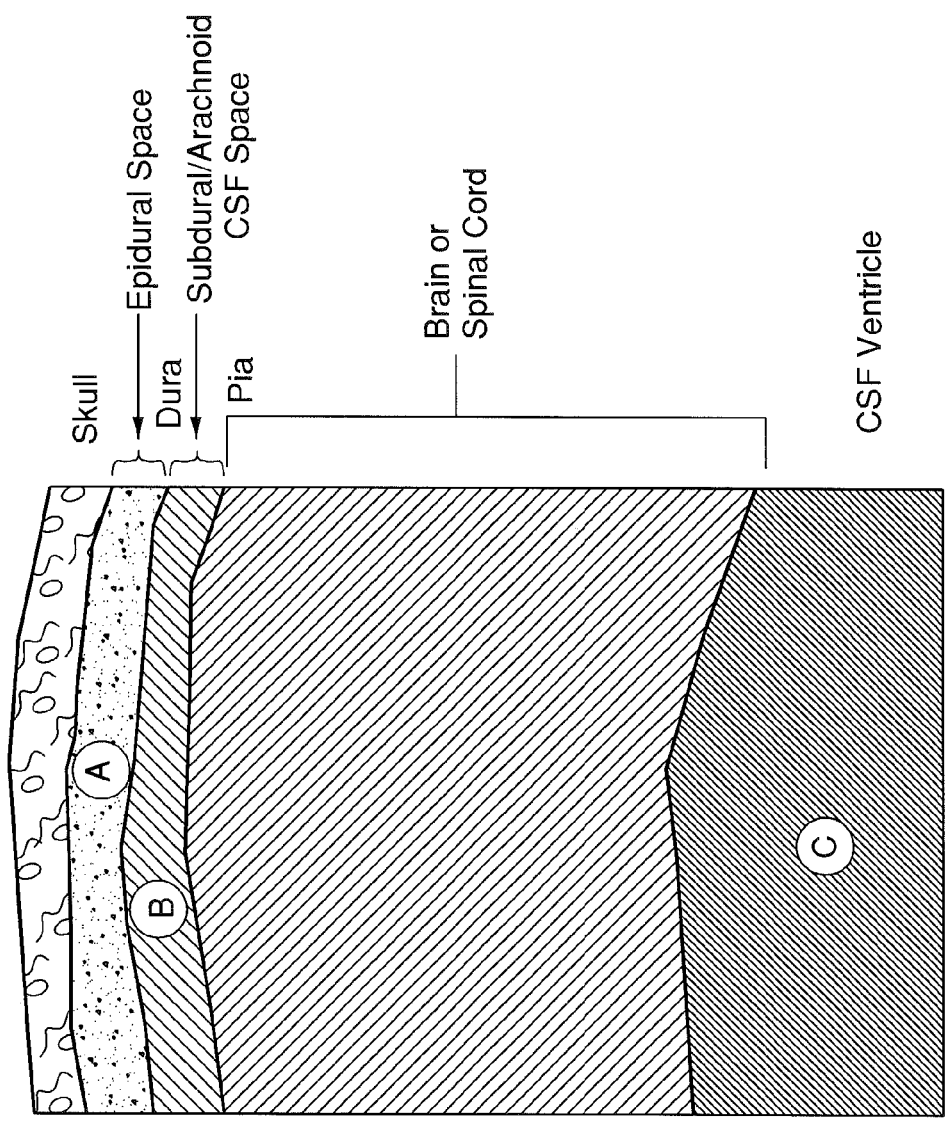
FIG. 6 is a schematic further illustrating the epidural and CSF spaces into which the oscillating compliance devices of the invention can be placed.

The oscillating compliance device is itself capable of being located in a number of places to affect the patient's intracranial capacity and compliance. For example, turning to FIGS. 4 and 5, the oscillating compliance device can be placed anywhere deemed appropriate by one with skill in the art within epidural space 2 or CSF space 3 of the patient's brain or epidural space 4 or CSF space 5 of the patient's spinal cord. The dimensions of the compressible composition of the oscillating compliance device are such that it fits within the epidural or CSF (i.e., subdural/arachnoid or brain ventricular) space of the brain or spinal cord (see FIG. 6). In one embodiment, the compressible composition is capable of being placed within the epidural space of the patient's brain and has a length of about 10 to about 50 millimeters (mm), a width of about 5 to about 20 mm and a thickness of about 4 to about 5 mm. Alternatively, in another embodiment, the compressible composition is capable of being placed within the CSF space of the patient's brain and has a length of about 5 to about 10 mm, a width of about 1 to about 10 mm and a thickness of about 1 to about 5 mm. In yet another embodiment, the compressible composition can be placed within the epidural space of the patient's spinal cord and has a length of about 10 to about 50 mm, a width of about 1 to about 10 mm and a thickness from about 1 to about 5 mm. In a further embodiment, the compressible composition placed within the epidural space of the patient's spinal cord is placed between the patient's L4 and L5 vertebral bodies. It may also be necessary to modify the size of the compressible composition such that it increases the patient's intracranial capacity at an effective level. Accordingly, one with skill in the art would preferably alter the dimensions of the compressible composition for a particular patient in order to suit the patient's specific treatment needs.

In another embodiment, the invention relates to an oscillating compliance system comprising two or more oscillating compliance devices. In a particular embodiment, the two or more oscillating compliance devices are used simultaneously. The oscillating compliance system comprises two or more of the passive oscillating compliance devices described above, that is, a system comprising two or more oscillating compliance devices having a compressible composition that is capable of free expansion and compression to affect an individual's ICC, CBF and/or ICP pulsatility. Any number of oscillating compliance devices can be used in the passive oscillating compliance system, the appropriate number determined by the skilled clinician and calculated based on the number of devices necessary to treat the patient adequately to increase intracranial capacity, compliance and cerebral blood flow. Thus, the number of oscillating compliance devices used in a particular patient may depend on the severity of the disease being treated, i.e., more devices may be required for a patient having a more severe disease.

In a further embodiment, the two or more oscillating compliance devices also comprise one or more reservoirs described above which can be placed in an extra cranio, spinal and/or subcutaneous location or within a body cavity.

Figure 7:
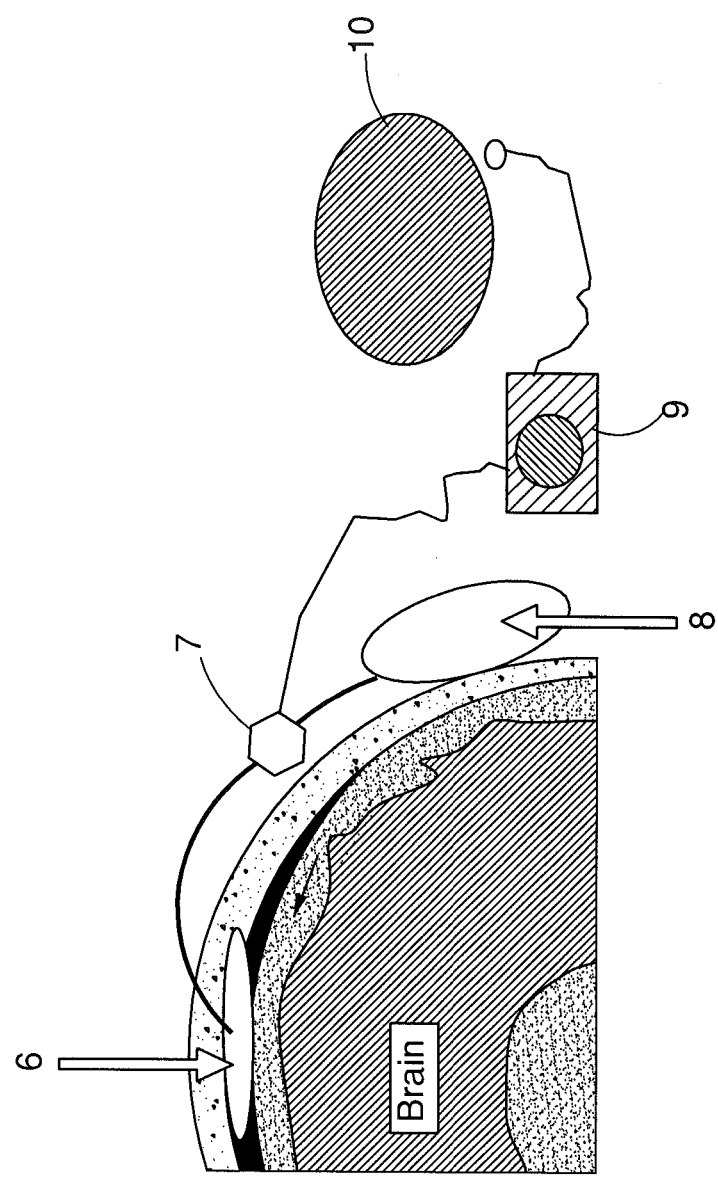
FIG. 7 is a schematic illustrating an embodiment of the oscillating compliance device having a pump coupled to a compressible composition and an external reservoir, the pump gaited to a biorhythm by a biorhythm sync to which it is connected.

The present invention also relates to an oscillating compliance device driven, not by the patient's ICP, but by a pump. In one embodiment, the pump is synchronized with a biorhythm of the patient. In this embodiment, the ICC of a patient is actively modulated (an active oscillating compliance device). Referring to FIG. 7, the oscillating compliance device is comprised of compressible composition 6, pump 7 coupled to compressible composition 6 for expansion and compression of compressible composition 6, reservoir 8 coupled to pump 7 and biorhythm sync 9 connected to pump 7, biorhythm sync 9 connected to the patient's biorhythm source 10. Thus, biorhythm sync 9 monitors biorhythm source 10 and triggers pump 7 to compress and expand compressible composition 6 in synchrony with the patient's biorhythm. Consequently, pump 7 actively compresses and expands compressible composition 6 in synchrony with the biorhythm (e.g., in synchrony with arterial blood), thereby increasing the intracranial space during systole with arterial blood inflow.

As used herein, a "biorhythm sync" is any suitable device which can monitor a biorhythm source in a patient and trigger the pump of the oscillating compliance device. For example, a biorhythm sync is an electrocardiogram (ECG or EKG) monitor which captures the electronic pulse wave (electrical rhythm, signal) of the heart and synchronizes the pump to that pulse. Devices that can act as biorhythm syncs and monitor a particular biorhythm are known and used in the art. For example, cardiac syncs which are commercially available (Datascope aortic balloon) are appropriate for use in the invention. As also used herein, a biorhythm source is any physiological rhythm which can be monitored. For example, a biorhythm source includes a pulse (e.g., an arterial pulse, such as a carotid pulse), cardiac rhythm (e.g., heart beat pressure and/or electrical pulse/rhythm) or an intracranial pulse.

In one embodiment, the compressible composition of the oscillating compliance device is a balloon catheter that is comprised of a substance (i.e., a fluid, gas or malleable substance). Like the compressible composition of the passive oscillating compliance device, that of the active oscillating compliance device can be any compressible composition suitable for use in a mammal containing any substance capable of being moved from one space to another by the force exerted by mechanical pump 7. The compressible composition can be comprised of a closed (e.g., a balloon catheter) or open system (e.g., an open catheter); in the open system, the compressible composition diverts a fluid substance (e.g., CSF or blood) to space (e.g., internal or external). The appropriate substance for use in the compressible composition, as deemed by one of skill in the art, will depend on several factors including the size and placement of the compressible composition and the patient's disease state. Though the volume of the substance required for use in the oscillating compliance device can be determined by one with skill in the art (e.g., based on the properties of the substance, the placement of the oscillating compliance device and the dimensions of the device necessary to adequately treat the patient), in a particular embodiment, the expansion and compression of the compressible composition displaces from about 0.5 to about 25 cc of the substance from the patient's internal space to the reservoir. In particular embodiments, about 0.75 to about 1.75 cc or about 1 to about 1.5 cc of the substance is displaced from the patient's internal space to the reservoir.

The active oscillating compliance device also has several other embodiments. In one embodiment, the reservoir is placed in an extra-cranio, spinal or subcutaneous location (e.g., the head or body) or placed within a body cavity (e.g., the pericardial or peritoneal sac). The appropriately-sized pump can be powered by a motor-powered battery able to provide the force required to compress and expand the compressible composition such that the substance therein is moved to and from the reservoir. The pump can also be powered by a physiologically-derived source, such as movement of a patient's body part (e.g., muscle structures or the heart muscle), movement of a patient's fluid (e.g., CSF or blood) or cardiovascular movement (e.g., heart muscle, aortic, hepatic or carotid vessel movement).

Figure 8:
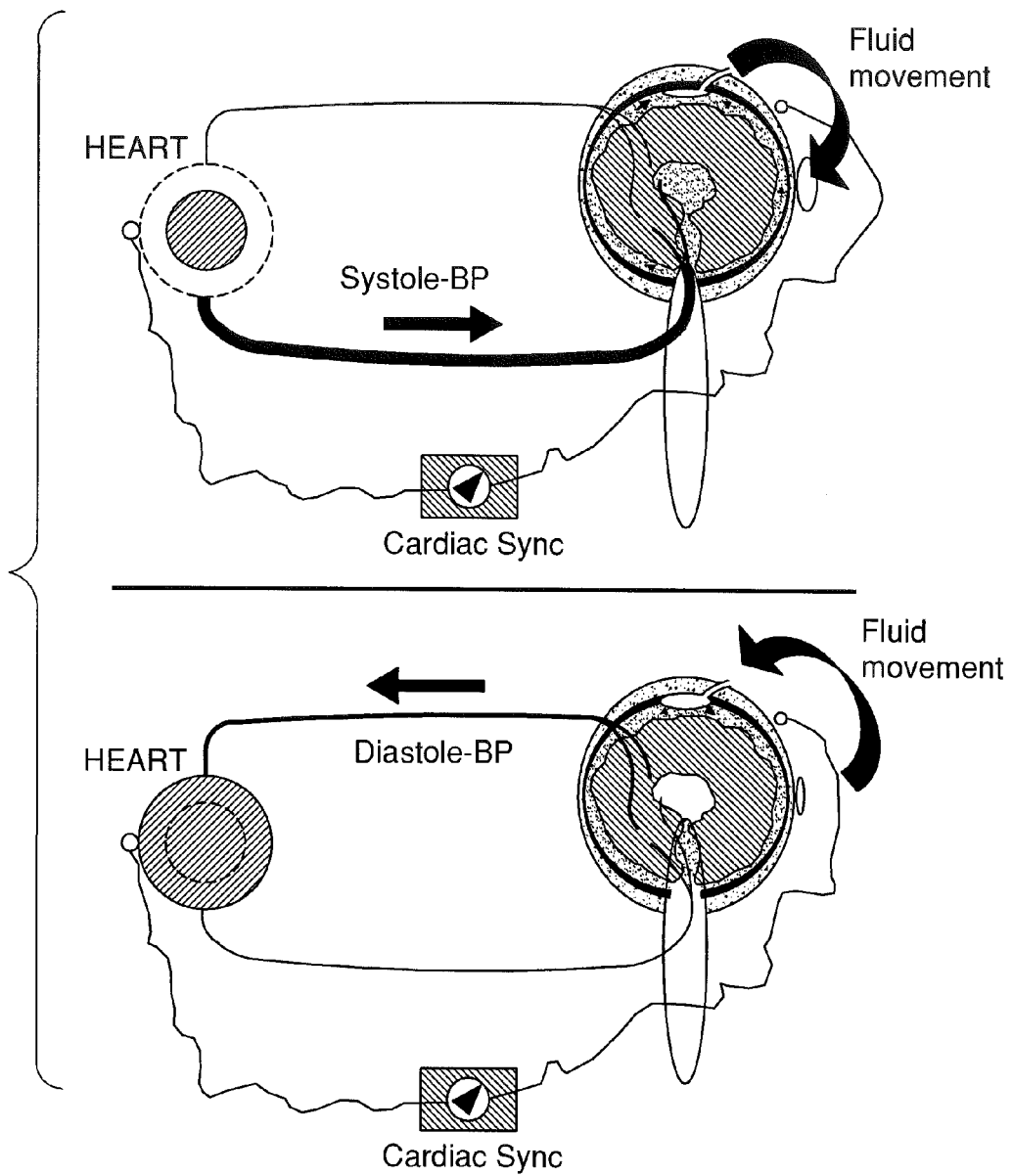
FIG. 8 is a schematic illustrating displacement of a substance from the compressible composition to an external reservoir during systole and return of the substance from the external reservoir to the compressible composition during diastole in an oscillating compliance device having a pump gaited to the heart by a cardiac sync.

In a particular embodiment, the source of the patient's biorhythm can be an electrical rhythm of the patient's heart, a cardiovascular pressure pulse, an ICP wave, or any source that appropriately facilitates arterial blood entry into the cranial cavity with the patient's arterial pulsations. In another embodiment, the biorhythm sync directing the pump is controlled by a microprocessor. The microprocessor can also be controlled externally (e.g., wirelessly) allowing one of skill in the art to, as necessary, alter the pump's compression and expansion of the compressible composition through the biorhythm sync according to the patient's needs. In a particular embodiment, the biorhythm source is the electrical rhythm of the patient's heart and the biorhythm sync is a cardiac sync. Thus, the pump's compression and expansion of the compressible composition and movement of the substance out of and into the compressible composition is gaited to the systole and diastole of the patient's heart (see FIG. 8). The pump and cardiac sync can be located either inside of or outside of the patient's body. Thus, in addition to being placed with the other components of the device inside of the patient's body, the sync can be connected to the oscillating compliance device but placed in a location outside on the patient's body (e.g., on or under the patient's skin) such that the sync is portable and/or wearable (e.g., on a belt) or placed outside the patient's body and located in non-portable place (e.g., on a machine or table).

The oscillating compliance device is capable of being placed within the epidural or CSF space (subdural/arachnoid or brain ventricular) of the patient's brain or spinal cord, the dimensions of which will vary according to the specific area in which the device is placed and can be determined by one with skill in the art. In one embodiment, the compressible composition capable of being placed within epidural space of the patient's brain has a length of about 10 to about 50 mm, a width of about 5 to about 20 mm and a thickness of about 4 to about 5 mm. In another, the compressible composition capable of being placed within the CSF space of the patient's brain has a length of about 5 to about 10 mm, a width of about 1 to about 10 mm and a thickness of about 1 to about 5 mm. In yet another embodiment, the compressible composition capable of being placed within the epidural space of the patient's spinal cord has a length of about 10 to about 50 mm, a width of about 1 to about 10 mm and from about 1 to about 5 mm. In a further embodiment, the compressible composition placed within the epidural space of the patient's spinal cord is placed between the patient's L4 and L5 vertebral bodies.

The active oscillating compliance device, like the passive device, can also be further comprised of an intracranial monitor and blood flow and/or oxygen probes. In one embodiment, the monitoring devices are in communication with a control system that can automatically adjust the pump's expansion and compression of the compressible composition based on the measurements of the monitoring devices. Hence, changes in the patient's ICP waveform or CBF due to treatment, disease state or other factors can be detected by the intracranial monitor, blood flow and/or oxygen probes and those changes registered and interpreted by the control system such that the pump can be adjusted manually or by the control system to regulate inflation and deflation of the compressible composition in real time, as needed to effectively change the measured parameters. The control system can be any one with an ability to perform the above tasks and is most preferably a microprocessor. The microprocessor can also be controlled remotely (e.g., wirelessly) to manipulate the pump's action.

The present invention further relates to an oscillating compliance system using the active oscillating compliance device described above. Thus, the invention relates to an oscillating compliance system comprised of two or more oscillating compliance devices having a compressible composition, a pump coupled to the compressible composition for expansion and compression of the compressible composition, a reservoir coupled to the pump and one or more biorhythm syncs connected to the pump of the one or more oscillating compliance devices. The biorhythm sync connects to one or more sources of a patient's biorhythm in order to synchronize the pump with the patient's one or more biorhythms. One or several devices may be used in a single patient for optimal ICP management. Although any number of oscillating compliance devices can be used in the system as deemed appropriate by one of skill in the art, it is more likely that no more than two active oscillating compliance devices would be employed simultaneously.

In one embodiment of the oscillating compliance system, the compressible composition of the two or more oscillating compliance devices is a balloon catheter comprising a substance capable of being moved from one space to another and is preferably a fluid, gas or malleable substance. In another embodiment, the one or more reservoirs of the two or more oscillating compliance devices is capable of being placed in any extra-cranio, spinal or subcutaneous space of the head or body or within a body cavity like the pericardial or peritoneal sac.

The oscillating compliance system can also be further comprised of an intracranial monitor, blood flow probes and/or oxygen probes to measure ICP, CBF and oxygen within the patient's cranial space, that are preferably in communication with and controlled by a microprocessor. In a preferred embodiment, the biorhythm sync is also in communication with and controlled by the microprocessor which can coordinate the expansion and compression of the compressible composition of the devices with both the one or more biorhythms and, as necessary, the measurements by the monitoring devices.

Figure 9:
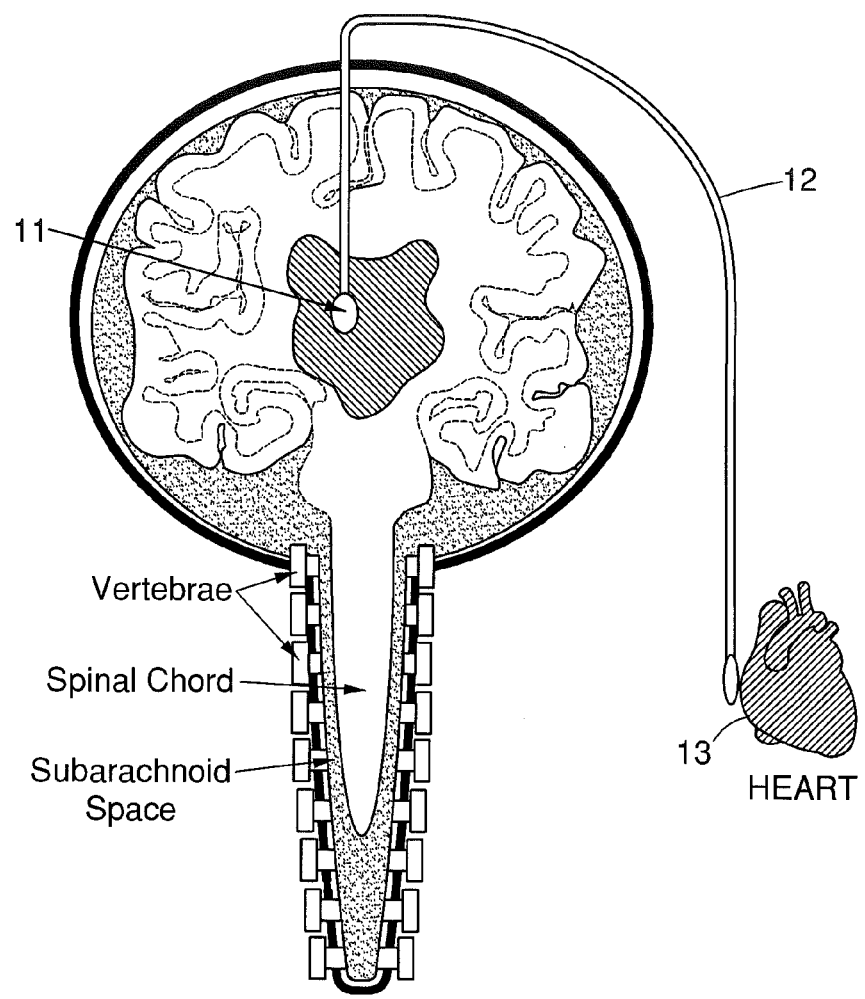
FIG. 9 is a schematic illustrating an embodiment of the oscillating compliance device having an external reservoir placed next to the heart, the external reservoir connected to a compressible substance by a tube.

The present invention further relates to an oscillating compliance device that derives its synchrony from a cardiac rhythm and its power to move a substance (e.g., a fluid) through the contractility of the heart itself. Thus, the oscillating compliance device is comprised of a compressible composition, a tube coupled to the compressible composition and a reservoir placed in a patient's pericardial space which is also coupled to the tube, the reservoir capable of free expansion and compression due to the contraction and expansion of the patient's heart. The reservoir can be comprised of any material that with appropriate tensile and elastic properties (e.g., plastic or silicone) such that it will compress due to the force generated by expansion of the heart and then expand due to the loss of that force when the heart contracts. Turning to FIG. 9, tube 12 of the device allows free exchange between compressible composition 11 and reservoir 13. In one embodiment, compressible composition 11 is a balloon catheter comprising any substance capable of movement out of the compressible composition, through tube 12 and back into compressible composition 11. As described herein, such substances can include fluids, gases or malleable substances appropriate for use of the device in a patient having a particular disease as determined by one with skill in the art. For example, when the heart contracts the reservoir (e.g., a thoracic balloon) expands, pulling a fluid from the compressible composition (e.g., a cranial balloon catheter) during systole. When the heart expands during diastole, the thoracic balloon is compressed, re-inflating and moving the fluid back to the cranial balloon catheter. In another embodiment, the compressible composition is comprised of an open system, the cardiac rhythm, via the reservoir, moving (i.e., diverting) fluid (e.g., CSF or blood) from the cranial or spinal cavities to a space (e.g., internal or external).

In one embodiment, the compressible composition of the oscillating compliance device can be placed anywhere within an epidural or CSF space of the patient's brain or the patient's spinal cord, wherever it is deemed to be most effective for the patient. For example, the compressible composition capable of being placed within the epidural space of the patient's brain would preferably have a length of about 10 to about 50 mm, a width of about 5 to about 20 mm and a thickness of about 4 to about 5 mm. The compressible composition placed within the subdural/arachnoid or brain ventricular space of the CSF space of the patient can have a length of about 5 to about 10 mm, a width of about 1 to about 10 mm and a thickness of about 1 to about 5 mm and the composition placed within the epidural space of the patient's spinal cord a length of about 10 to about 50 mm, a width of about 1 to about 10 mm and a thickness from about 1 to about 5 mm. In a preferred embodiment, the compressible composition placed within the epidural space of the patient's spinal cord is placed between the patient's L4 and L5 vertebral bodies.

The oscillating compliance device can be further comprised of intracranial monitor, blood flow probes and/or oxygen probes to measure ICP, CBF and oxygen within the patient's cranial space. These intracranial monitors allow the skilled clinician to monitor any alterations in ICP or CBF and, consequently, the effectiveness of the therapy.

The present invention also relates to a method for protecting an individual's brain from arterial pulsations that enter the individual's cranial cavity such that abnormal transmissions of arterial pulsations to the individual's brain capillaries and tissue are reduced or eliminated. The method comprises displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression.

In one embodiment, the compressible composition is a balloon catheter comprised of a movable, transferable substance, the substance being a fluid, gas or malleable substance. In another embodiment, the one or more oscillating compliance devices comprise a reservoir and the substance is displaced to this reservoir during systole. The reservoir, made of any material with an ability to elastically expand and deflate, is, in a particular embodiment, coupled to the internal compressible composition. The reservoir could be placed in several places in the patient's body including, extra-craniospinally, subcutaneously or within a body cavity. In one embodiment, the reservoir is placed in a subcutaneous space in the head or body and in another, it is placed within a body cavity such as the pericardial or peritoneal sac.

In another embodiment of the method, the one or more oscillating compliance devices derive their synchrony and operative ability from the heart's contractility. Thus, in this embodiment, the one or more oscillating compliance devices further comprise a tube connecting the compressible composition to the reservoir which is placed within the pericardial sac. The reservoir is capable of free expansion and compression due to the contraction and expansion of the individual's heart, the expansion and compression of the reservoir thereby causing the displacement of the substance from and the return of the substance to the compressible composition.

In yet another embodiment of the method, the one or more oscillating compliance devices is of the active type, the devices further comprised of a pump coupled to the compressible composition and to the reservoir and a biorhythm sync connected to the pump, the biorhythm sync for connecting to a source of the individual's biorhythm. The biorhythm sync monitors the individual's biorhythm and synchronizes the pump's expansion and compression of the compressible composition with that biorhythm, thereby causing the pump of the one or more oscillating compliance devices to displace a substance from and return the substance to the compressible composition. The biorhythm sync preferably is in communication with a control system like a microprocessor. The biorhythm source can be any biological rhythm timed to arterial blood pulsations and in one embodiment is an electrical rhythm of the heart, cardiovascular pressure or an ICP wave. In a particular embodiment, the biorhythm source is an electrical rhythm of an individual's heart and the biorhythm sync is a cardiac sync. The cardiac sync can be placed either inside of or outside of the individual's body and can be any cardiac sync known in the art. Gaited to the biorhythm through the biorhythm sync, the pump of the one or more oscillating compliance devices can be powered by a motor battery or by some physiologically-derived power (e.g., movement of a body part, bodily fluid or cardiovascular movement).

The compressible composition of the one or more oscillating compliance devices for use in the method are capable of being placed within an epidural or CSF space of the individual's brain or spinal cord. The dimensions of the compressible composition can be determined by one with skill in the art such that the composition fits appropriately in the epidural or the subdural/arachnoid or brain ventricular CSF space of the individual's brain or spinal cord and can adequately treat the individual. For example, in one embodiment, a compressible composition capable of being placed within an epidural space of the individual's brain can have a length of about 10 to about 50 mm, a width of about 5 to about 20 mm and a thickness of about 4 to about 5 mm. In another embodiment, a compressible composition capable of being placed within the CSF space of the individual's brain can have a length of about 5 to about 10 mm, a width of about 1 to about 10 mm and a thickness of about 1 to about 5 mm. In yet another embodiment, the compressible composition can be placed within the epidural space of the individual's spinal cord and has a length of about 10 to about 50 mm, a width of about 1 to about 10 mm and a thickness from about 1 to about 5 mm. In a further embodiment, the compressible composition placed within the epidural space of the individual's spinal cord can be located between the patient's L4 and L5 vertebral bodies.

The method can further comprise measuring the individual's ICP, CBF or oxygen levels using an intracranial monitor, blood flow probe(s) and/or oxygen probe(s). A control system in communication with the pump can then, in one embodiment, adjust the one or more pumps' expansion and compression of the compressible composition based on the individual's ICP, CBF or oxygen levels measured. In one embodiment, the control system is a microprocessor which can also be controlled wirelessly.

The invention also relates to methods that address several aspects of intracranial hydrodynamics. The methods identify these various problems of intracranial hydrodynamics caused by a number of diseases of conditions, all of which can be remedied by displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of free expansion and compression. The methods then affect ICC, CBF and/or ICP pulsatility/waveform.

For example, the invention relates to a method to increase ICC in an individual. In order for blood to enter the closed space of the cranium, the brain must be compliant, a condition dependent on the brain's capacity to accommodate changes in volume which allows for the proper buffering of arterial pulsations. When the Windkessel mechanism breaks down, due to neurologic disease, for example, the brain becomes non-compliant. Thus, the method of the invention recreates the Windkessel effect, increasing ICC in an individual by displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression.

In addition, the method of the invention relates to modulating the size of the CSF space. Normally, the brain has a high plasticity and the volume of the CSF space can be altered by many factors, including increased cerebrospinal fluid or increased pressure. However, in many disease states, like hydrocephalus, for example, sustained alterations to the CSF space can have a negative on the brain (e.g., by increased CSF fluid volume and/or decreased CBF). Thus, the present invention also relates to a method of controlling the size of an individual's CSF space in synchrony with incoming arterial pulsations by displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression. In a particular embodiment, the method is employed in neurologic disease states but could also be used in individuals without disease in which modulation of the size of the CSF space is desired (e.g., global vascular deficiency in aging).

The method also relates to increasing the volume capacity of the thecal sac to better allow entry of arterial blood into the cranial cavity. The brain is enclosed within a rigid skull, which causes the cerebrovascular system to be more vulnerable to incoming arterial pulsations; however, these pulsations are primarily buffered by the thecal sac. In a variety of conditions, including aging, cerebrovascular disease, brain atrophy and post-brain hemorrhage and infection, compliance of the thecal sac is compromised. Hence, the present invention also employs the method, increasing the volume capacity of an individual's thecal sac to facilitate the entry of arterial blood into the individual's cranial cavity by displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression. Increase of the thecal sac volume capacity is accomplished at the moment and duration of incoming arterial pulse waves, the oscillating compliance device acting as a dynamic absorber of CSF pulsations.

The method can be further used to alter arterial blood pulsations in an individual's brain. There are several factors that can influence the speed and force of arterial blood pulsations in the brain. Typically, the pulsations have a minimal impact on the brain as, through the Windkessel effect, the brain sees a nearly continuous, even capillary blood flow. However, under aberrant conditions like acute or chronic neurologic disease states, disruptions of arterial blood pulsations and uneven blood flow occur. Accordingly, the present invention relates to a method of altering arterial blood pulsations in an individual's brain by displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression. The method can be used to both correct pulsatility abnormalities and/or improve brain function.

The present invention also relates to a method to alter (e.g., increase or decrease) cerebral blood flow. Decreased ICC and/or increased CSF volume or pressure cause vascular impedance, that is, decreased cerebral blood flow and, consequently, decreased cerebrovascular circulation. Decreased CBF characterizes several vascular and brain disorders and this loss of blood in the brain damages the brain tissue due to a decrease in the amount of oxygen that is normally delivered to the brain tissue. Accordingly, the present invention further relates to altering the efficiency of an individual's cerebral blood flow and cerebrovascular circulation by modulating the individual's intracranial space by displacing a substance from a compressible composition in the individual's intracranial or intraspinal space during systole using one or more oscillating compliance devices and returning the substance to the compressible composition in the individual's intracranial or intraspinal space during diastole using the one or more oscillating compliance devices, wherein the compressible composition is capable of expansion and compression.

The invention also relates to a method of treating a patient having altered ICC, CBF or ICP pulsatility by implanting the oscillating compliance devices or oscillating compliance systems of the invention. In diseases like congestive heart failure, cartoid endarterectomy and during cardiopulmonary bypass surgery, ICP pulsatility (and CBF) is lower than what is normal and/or desired. For example, during cardiopulmonary bypass surgery, a rotary pump ensures a constant flow of blood during the operation; however, this constant flow of blood due to the rotary pump is non-pulsatile, in other words, pulsatility is decreased. Thus, the OCD can also be used to increase cerebral blood flow and ICP waveform. Alternatively, in diseases like dementia (e.g., Alzheimer's, vascular dementia, normal pressure hydrocephalus), hydrocephalus and during vasospasms, ICP pulsatility is higher than normal and, in this case, the OCD can be used to decrease ICP waveform.

In normal aging, as well as in several neurological conditions, decreases in ICC allow the direct transmission of arterial pulsations to the brain without CSF buffering protection. There are a number of hydrodynamic brain disorders that can be treated with one of the oscillating compliance devices of the invention, including hydrocephalus, stroke, dementia, migraine headaches and any other diseases in which decreased ICC is apparent or suspected.

Hydrocephalus is characterized by an abnormal rise in CSF volume that was traditionally thought to be caused by an imbalance of CSF production and absorption. However, many now believe hydrocephalus occurs due to a restriction in arterial blood flow (Geitz, *Neurosurg Rev,* 27:145-165, 2004). Thus, in one embodiment, the method is used to treat hydrocephalus disorders that include chronic hydrocephalus, normal pressure hydrocephalus, pseudotumor cerebri and slit ventricle syndrome. Another hydrodynamic disorder, stroke, is a disease that manifests in a number of ways, all of which generally involve brain hemorrhage and/or swelling that causes decreased cerebral blood flow and decreased intracranial compliance. Thus, in another embodiment, the method is employed to treat patients who have a variety of types of stroke including, chronic stroke, microvascular disease, dementia, Moya-Moya, multiple infarct disease, posterior circulation insufficiencies and Binswanger disease. Similarly, dementia has also been identified as a disease state that is characterized by decreased ICC. Increased arterial pulsatility injures the brain capillary tissue, resulting in a decreased cerebrovascular flow efficiency which is thought to be partially responsible for the reduced brain function observed in dementia. Accordingly, in yet another embodiment, vascular dementia, Alzheimer's disease and normal pressure hydrocephalus can be treated with one of the oscillating compliance devices in the method. Interestingly, migraine headaches have been found to display characteristics that indicate the headaches could be alleviated by increasing ICC. The brains of those with migraine headaches show a distortion of intracranial blood vessels, dysynchrony of arterial blood flow and CSF pulsatility disturbances. Hence, in yet another embodiment, migraine headaches are treated using the method, the types of migraine headaches treated being both pediatric and adult migraines and those migraines that are intractable.

EXEMPLIFICATION

The foregoing examples of the invention are intended solely to be exemplifications of the invention and are non-limiting examples regarding the various embodiments the invention encompasses.

Prophetic Example 1

Experimental Testing of Oscillating Compliance Device

Balloon Design

Balloon catheters are designed and created to meet the specific design parameters (i.e., shape, volume displacement) and activation (i.e., frequency, amplitude, duration) with the cardiac cycle prior to in vivo experimental animal testing. A prototype of the balloon catheter is shown in FIGS. 10 and 11. The design parameters will vary based on placement of the balloon catheter in an epidural or CSF space of a subject's brain or spinal cord. For example, the dimensions of a balloon catheter for use in the epidural space of the individual's brain could encompass a length of about 10-50 mm, a width of about 5-20 mm and a thickness of about 4-5 mm. Those dimensions for a balloon catheter placed within the CSF space of a subject's brain could be a length of about 5-10 mm, a width of about 1-10 mm and a thickness of about 1-5 mm and those for a balloon catheter placed within the epidural space of the individual's spinal cord would have estimated dimensions of a length of about 10-50 mm, a width of about 1-10 mm and a thickness of less than about 1 mm.

Oscillating Compliance Device Evaluation

The effectiveness of the oscillating compliance device on cerebrovascular blood flow and CSF pulsatility is evaluated in vivo using an animal model as described (Johnson M J et al., *J. Neurosci Methods* 91:55-65, 1999). Briefly, a suboccipital craniectomy is performed stereotactically to allow visualization of the dorsal cerebellar vermis and brain stem. Using bipolar cautery, suction, and retraction a small opening is made in the dura and arachnoid membrane allowing visualization of the floor of the fourth ventricle through which a flexible silicon catheter tubing (1.5 mm O.D.) connected to an 18-gauge angiocath and syringe is inserted. The catheter is then inserted into the fourth ventricle, and 0.50 mL of cyanoacrylic gel is injected. The catheter is then cut and left in the open position. The dura is sutured and all the muscle layers closed in a layered fashion with interrupted sutures.

Five (n=5) young adult animals, canine familaris weighing 25-30 kg are used. Data on cerebral blood flow (CBF) is obtained from the animals using two independent methods: transcranial Doppler ($CBF_{TCD}$ and cerebral microsphere injection ($CBF_{MI}$).

Microspheres ($CBF_{MI}$): Microspheres injected into the circulating blood flow can be used to determine cerebral blood flow. Regional blood flow is proportional to the number of microspheres trapped in the microvasculature in the tissue region of interest (Hyemann et al., *Prog. Cardiovasc. Dis.,* 1977). Stable isotope labeled microspheres (non-radioactive) are used (BioPAL™, BioPhysics Assay Laboratory, Inc.). At the time of sacrifice, tissue samples to determine CBF are collected from eight regions (inferior frontal, superior temporal, anterior/posterior medial, occipital, cerebellum and caudate nucleus) from the right hemisphere in each animal and processed by BioPAL.

Transcranial Doppler ($CBF_{TCD}$): In addition to the $CBF_{MI}$ method, TCD are employed to estimate more dynamic changes in CBF mean/peak velocity, intensity (see FIG. 12, TCD). With a 2 MHz pulsed-wave Doppler (Multidop T, DWL-Compumedics, Sipplinggen, Germany) insonation of the caudal cerebral artery, which is comparable to the intracranial part of the internal carotid artery in humans is performed transtemporally. The pulse repetition frequency (PRF) is fixed at 3 kHz, and the maximal spatial peak-tempral averaged intensity (SPTA) will be 100 mW/cm$^2$, corresponding to p=0.27 hPa (peak refraction pressure). Doppler frequency spectra are recorded at a depth of 42-44. Signals are obtained digitally, stored and analyzed on computer via software provided by CCF Department of Radiology. Reference flow velocities for normal values can be taken from Transcranial Doppler Ultrasonography, (eds. Babilian V L, Wechsler L R. Mosby Yearbook, Inc. 1993).

In addition, data is collected on intracranial compliance, CSF pulsatility (cranial and spinal), arterial blood (ABPp) and venous blood pulsatility (VBPp) and cardiac output (CO). Chronic condition: CBF and CSFp data is collected intraoperatively before CH induction (baseline) so that each animal serves as its own control. Acute condition: CBF and CSFp is monitored during acute manipulations that include: (1) hyperventilation; (2) CSF removal and (3) CSF infusion before, during and after OCD activation. In order to confirm the severity or degree of chronic hydrocephalus (CH), 3D volumetric MRI and ICP monitoring are obtained. The results are then correlated with other patterns of change such as CBF, CSFp and ICC.

Cranial ICP: A small twist-drill hole is made for subdural microsensor insertion to monitor ICP (Codman Camino Microsensor, Raynham, Mass.) (see FIG. 12, ICP(1)). The same burr hole is used to insert a ventricular catheter to allow access to the CSF compartment enabling intracranial compliance to be measured. Using a modification of the Massermann technique, CSF (0.2 cc) are withdrawn and infused to decrease and increase ICP respectively.

Spinal ICP: A second ICP microsensor and ventricular catheter are inserted into the CSF lumbar cistern (L4-L5) of the spine (see FIG. 12, ICP(2)). This allows the independent and/or simultaneous monitoring of ICP pulsatility forces during evaluation of the oscillating compliance device.

Arterial and Venous Pressure/Pulsatility: In addition, the internal carotid artery (ABP) and the internal jugular vein (VBP) are catheterized (20 gauge angiocatheter) and monitored via a pressure transducer to obtain pulsatility waveforms. All intra-operative monitoring are collected online and realtime via multimodel data acquisition system (ADInstruments, PowerLab version 5.3.2). This allows for the simultaneous collection and analysis of ICP (cranial or spinal), ABP and VBP data sets.

Oscillating Compliance Device Implantation

Figure 12:
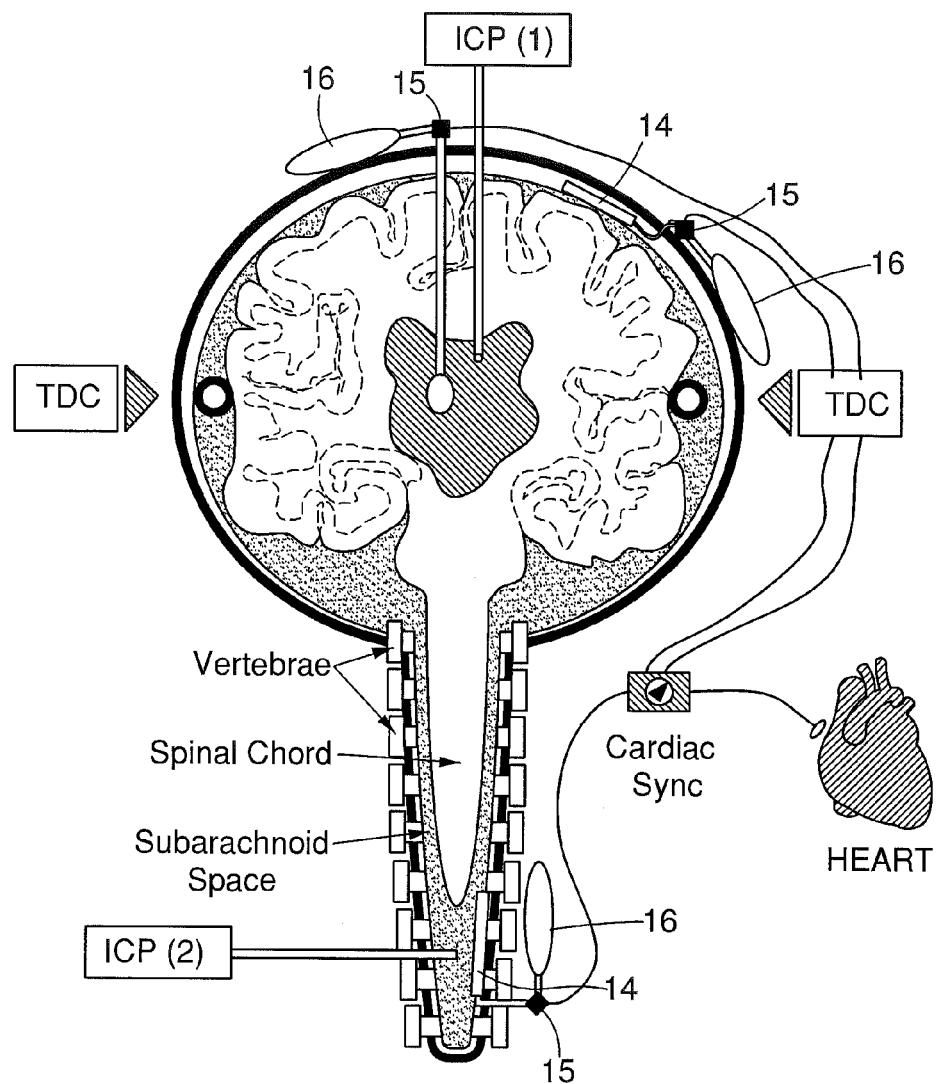
FIG. 12 is a schematic illustrating the testing and monitoring of oscillating compliance devices in vivo.

The oscillating compliance device is tested as shown in FIG. 12. The device is placed in the brain or the spinal cord, balloon catheter 14 coupled to pump 15 and subcutaneous reservoir 16, pump 15 connected to the cardiac sync, which connects to the animal's heart. Commercially available intra-aortic pediatric balloon catheters (Datascope Corp., #0686-DM-0116-01) are modified in a polymer lab to accommodate the parameters (i.e., volume, shape) identified during in vitro testing. In brief, a small twist-drill hole (5 mm) is made unilaterally above the dorsolateral convexity of the parietal cortex. The balloon catheter is placed through this burr hole into the epidural space, and connected to an intra-aortic pump (Datascope Corp. CS100, Intellisync IAB pump, #0020-00-0463-01). Similarly, modified spinal balloon catheter 14 is inserted into the epidural space adjacent to the lumbar cistern via L4-L5 vertebral bodies. Both the cranial and spinal oscillating compliance devices are left in place after chronic hydrocephalus induction surgery. The oscillating compliance device is activated intraoperatively when CBF and CSFp measures are obtained at baseline and 30 days post-CH induction.

Sacrifice, Tissue Preparation, Histology and Immunochemistry

All animals are deeply anesthetized with sodium pentobarbital in combination with inhaled isoflorane and perfused via bilateral catheterization of the carotid arteries with 4% paraformaldehyde (PFA) in 0.1M PBS, pH=7.4. The brains are removed, post-fixed for 24 hours in 4% PFA and cryoprotected in graded sucrose solutions for study of gross pathology, frozen sectioning, and routine histology (H&E, cresyl violet) and immunohistochemical analyses for biocompatibility.

Example 2

Oscillating Compliance Device Fabrication

Figure 13A:
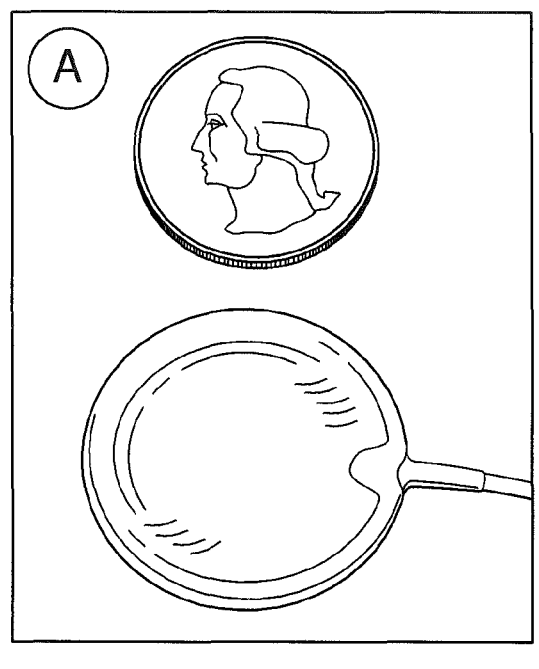
FIGS. 13A-13B are pictures of an alternate design of a compressible composition of an oscillating compliance device.
Figure 13B:
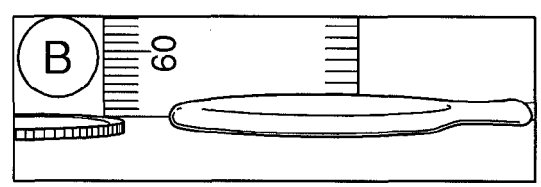
Figure 14:
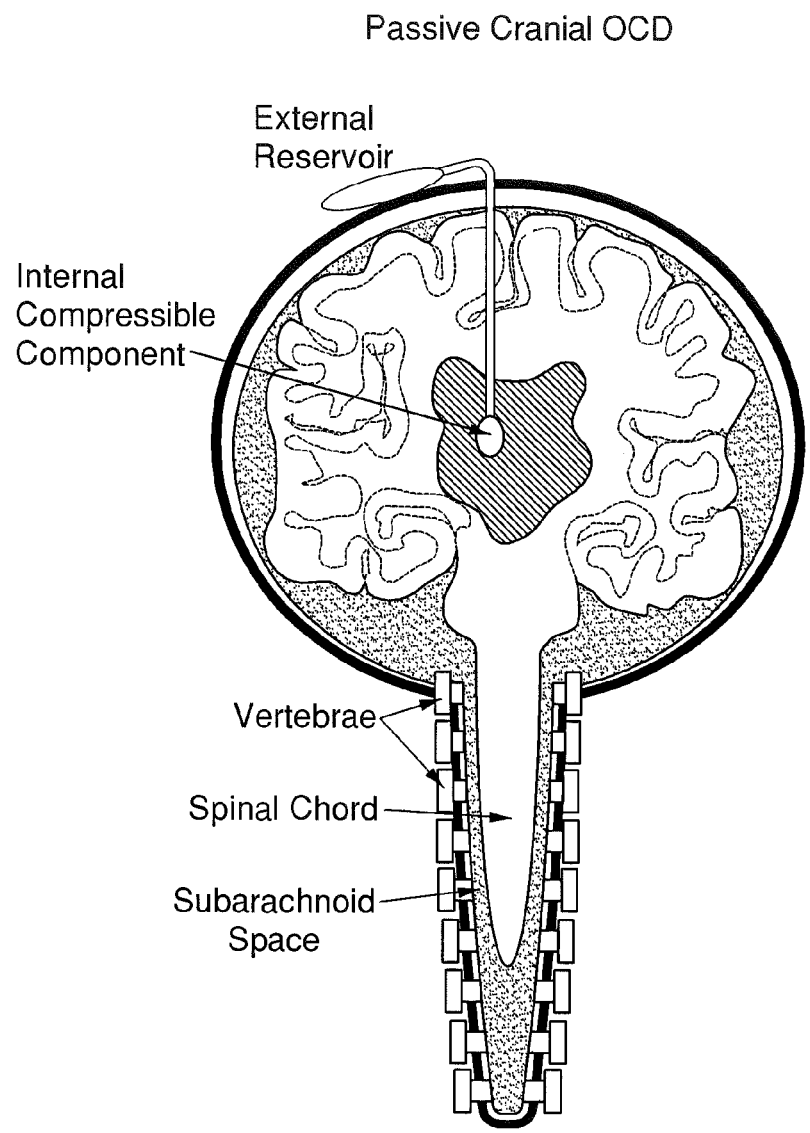
FIG. 14 is a schematic illustrating a passive cranial oscillating compliance device.
Figure 15:
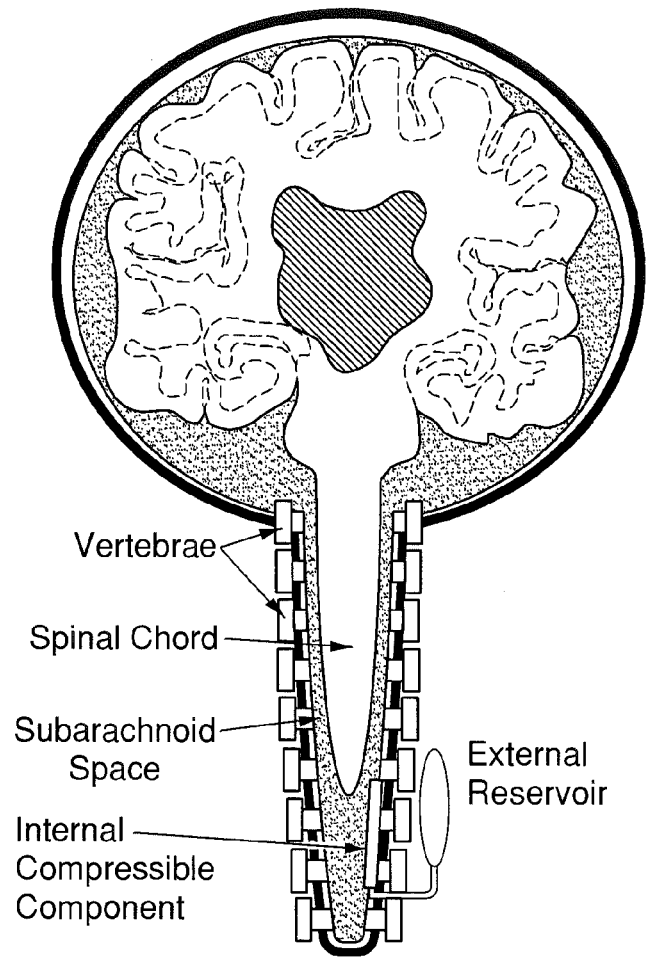
FIG. 15 is a schematic illustrating a passive spinal oscillating compliance device.
Figure 16:
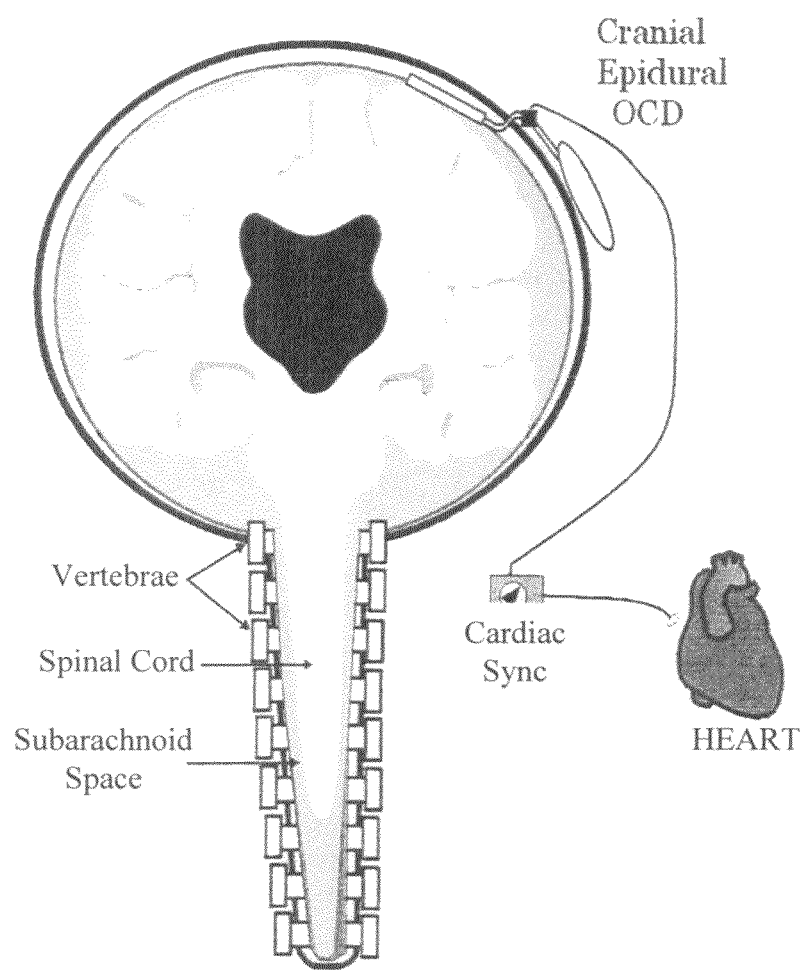
FIG. 16 is a schematic illustrating an active cranial epidural oscillating compliance device.
Figure 17:
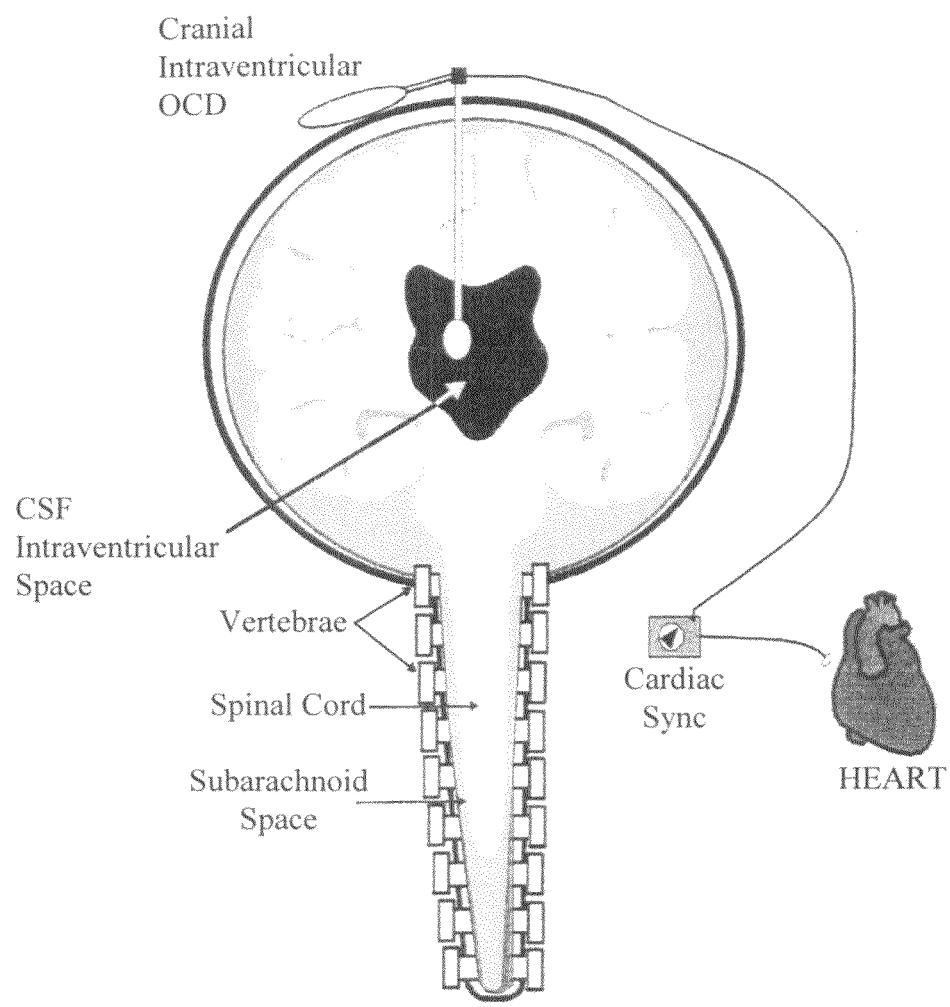
FIG. 17 is a schematic illustrating an active cranial CSF intraventricular oscillating compliance device.
Figure 18:
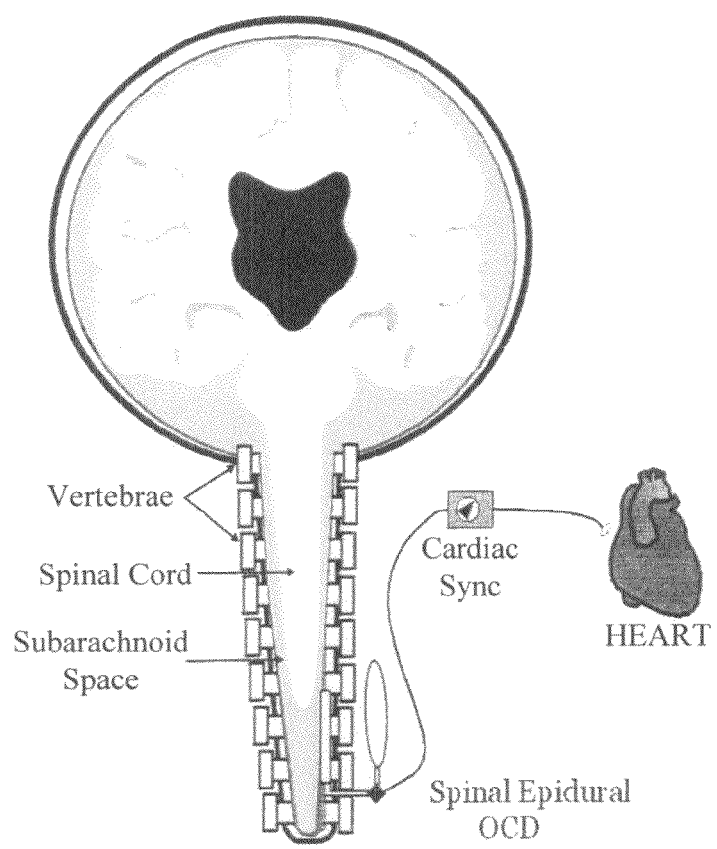
FIG. 18 is a schematic illustrating an active spinal epidural oscillating compliance device.
Figure 19:
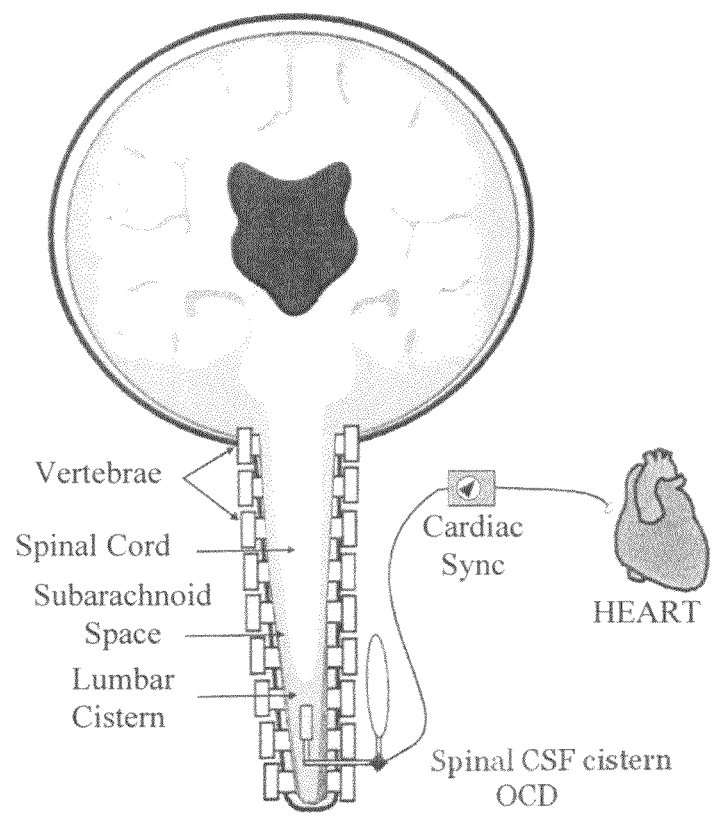
FIG. 19 is a schematic illustrating an active spinal CSF oscillating compliance device.

One embodiment of a working OCD as shown in FIGS. 13A-B was fabricated by the following methods:

Method 1

1. Sizing study: A PVC balloon was made based on the size and volume estimation (predetermined) using a PVC film by heat sealing. Ten centimeter PVC pressure tubing (Becton Dickinson PT06) was bonded with the female end, as a port by using polyurethane adhesive.
2. SLA (stereolithography) mandrel design and build: The internal dimension of a circular or spherical balloon was built based on satisfaction of the sizing study design. The disk shape design needed to fit the requested volume, dimension and properties for solution casting. A solid model was created with Pro/Engineer and the disk built with SLA using a UV cured resin.
3. Silicone rubber/Plaster mold making: The UV cured resin disk was polished and one half of the disk was cast with silicone rubber (P50, Silicone Inc.) while the other half was cast with plaster.
4. Clay mandrel fabrication: The silicone half of the mold was filled with wet clay which was used for ceramic making. The plaster half of the mold was pressed onto the clay filled silicone part and the clay allowed to dry. The mold was opened and the clay disk removed. The clay disk was then polished. A hole was made on the clay disk and a pin inserted and bonded as the mandrel of the balloon port. The disk was coated with a thin layer of egg yolk and allowed to dry. The coated clay disk was the mandrel of the pancake balloon (epidural OCD).
5. Polyurethane solution casting (Dip coating): A polyurethane solution casting (dip coating) was prepared: 10% ChronoFlex® AR: Biodurable Medical Grade Polyurethane (Cardiotech International, Inc.). The mandrel was dipped into the Chronoflex solution and rotated in a bi-axial rotating setup to allow the solution to flow evenly on the mandrel surface. The rotating setup was placed in a 60° C. oven to evaporate the solvent (Dimethyl Acetamide, DMAC) from the Chronoflex solution. Each coat needed 2 to 4 hours to dry and the process required 4 to 6 coats to build up the thickness. Thereafter, the coated mandrel was left in the oven for 24 hours for fully drying or curing.
6. Clay mandrel removal: The pin was removed from the mandrel by pulling and submerge the no-pin mandrel in water. The water was allowed to be absorbed into the clay to soften it. The softened clay was squeezed out from the port and balloon and the internal surface of the balloon cleaned. The balloon was tested for leaks by filling it with air.
7. Balloon/Catheter assembling. The cleaned balloon was placed in the 60° C. oven to dry. The port edge was trimmed to keep a port length of 5 to 10 mm. The Chronoflex AR was applied on the bonding area of the catheter, and then inserted into the port. The balloon catheter was placed in 60° C. oven for 2 hours.

Method 2

1. Silicone rubber mold making: One half of the polished UV cured resin SLA disk was cast with silicone rubber (P50, Silicone Inc.) and the other half with semi-transparent silicone rubber (MDX4-4210, Prosthetic Silicone Elastomer) to make a set of silicone mold.
2. Low melting point alloy mandrel fabrication: The low melting point alloy (LMA 158, Small Parts, Inc.) was melted at 70-75° C. The melt alloy was then cased to the silicon mold with the port pin. When necessary, defects were filled with acryl-Green Spot Putty (3M, #05114-5960) and the filled alloy mandrel polished with #400 sandpaper. The polished mandrel was dip coated with 5% PVA (Polyvinyl alcohol, DU PONT Grade Chronoflex solution) and the dipped mandrel rotated in a bi-axial rotating setup to allow the solution to flow evenly on the mandrel surface. The rotating setup was in a 60° C. oven to evaporate the solvent, Dimethyl Acetamide (DMAC) from the Chronoflex solution. Each coat needed 2 to 4 hours to dry, and 4 to 6 coats to build up the thickness. Thereafter, the coated mandrel was kept in the oven for 24 hours for fully drying or curing.
3. Polyurethane solution casting (Dip coating): The Dip coating was prepared: 10% ChronoFlex® AR: Biodurable Medical Grade Polyurethane (Cardiotech International, Inc.). The mandrel was dipped into the Chronoflex solution and rotated in a bi-axial rotating setup to allow the solution to flow evenly on the mandrel surface. The rotating setup was placed in a 60° C. oven to evaporate the solvent, Dimethyl Acetamide (DMAC) from the Chronoflex solution. Each coat needed 2 to 4 hours to dry, and 4 to 6 coats to build up the thickness. Thereafter, the coated mandrel was kept in the oven for 24 hours for full drying or curing.
4. Removal of the alloy mandrel: The Chronoflex AR coated mandrel was submerged into 70-75° C. water to melt the alloy. The port pin was pulled out, allowing the melted alloy to flow out through the port. The balloon was kept in 60° C. water for 2 or more hours until the PVA dissolved totally. The internal surface of the balloon was rinsed to remove the PVA and the remains of the alloy particle using 40 to 60° C. warm water. The balloon was then filled with air to test for leaks. Thereafter, the balloon was allowed to dry in a 60° C. oven.
5. Balloon/Catheter assembling: The port edge was trimmed to keep the port length to 5 to 10 mm. The Chronoflex AR was applied on the bonding area of the catheter which was then inserted into the port. The balloon catheter was placed in a 60° C. oven for 2 hours.

Example 3

Animal Model of Chronic Hydrocephalus (CH)

An experimental animal model of chronic obstructive hydrocephalus produced a gradual increase in ventricle size, which was well tolerated, producing transient and subtle clinical effects. Unlike previous models, there was no focal compression or general inflammation, which may confound analysis. Because of the animal size, this model allows clinically relevant measurements of CBF, CSF hydrodynamics (i.e., volume and pressure), intracranial compliance, and their relationship to CSF and brain pathology.

Figure 20:
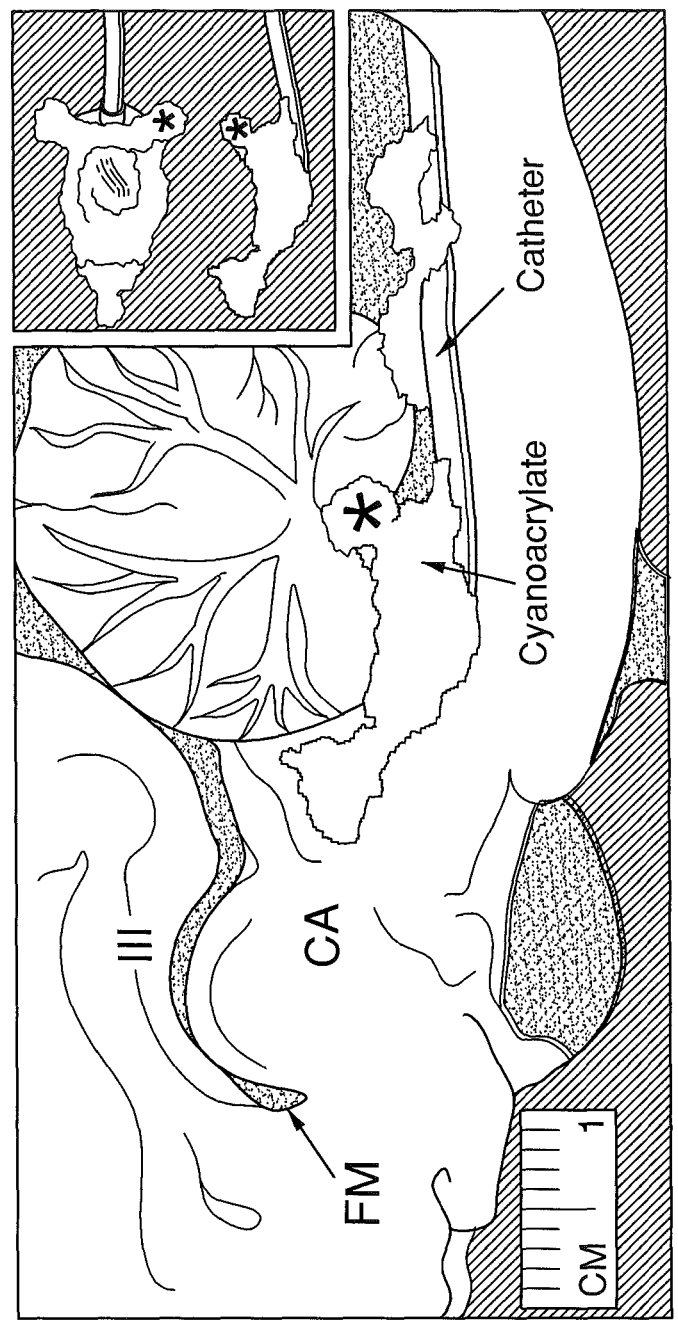
FIG. 20 is a picture showing the sagittal view of a canine brain in which hydrocephalus was surgically induced via injection of cyanoacrylate into the $4^{th}$ ventricle. (FM=foramen of Monro; III=$3^{rd}$ ventricle; CA=cerebral aqueduct.)

Chronic obstructive hydrocephalus was induced in adult mongrel canines by surgically obstructing the posterior cerebral aqueduct and fourth ventricle through the insertion of a catheter and injection of cyanoacrylate gel (0.4-0.6 cc) (see FIG. 20). A small occipital craniectomy allows the posterior fossa to be exposed, allowing visualization of the cerebellar vermis, dorsal brainstem, and spinal cord, and the arachnoid membrane overlying the foramen of Magendie at the base of the $4^{th}$ ventricle opened. Cyanoacrylate gel was injected into the body of the $4^{th}$ ventricle through a flexible silicone catheter connected to a 1 cc syringe.

Clinically, animals have typically shown a transient increase in lethargy, appetite loss, and demonstrate some hind limb ataxia. A neurological exam and clinical index was developed for monitoring recovery and outcome. No animals showed persistent focal neurological deficit, although long term changes in irritability reactiveness were sometimes noted. This experimental model has proven to be extremely useful in the investigation of hydrocephalus, the mechanisms underlying the cause and progression of this disorder and cerebral ischemia/hypoxia, and adaptive responses relating to treatment effects of CSF diversion (i.e., shunting). This experimental model has increased understanding of the processes relating to acute versus chronic hydrocephalus, and differences in cerebral blood flow, oxygen delivery, and CSF hydrodynamics (e.g., production, clearance, and turnover) and content, as well as mechanisms relating to cerebral adaptation. Further, this model, can be used to directly address questions that may arise in the clinical setting, study them in a controlled laboratory environment, develop new treatments and/or protocols, and ultimately implement these findings back into the clinical arena.

Figure 21:
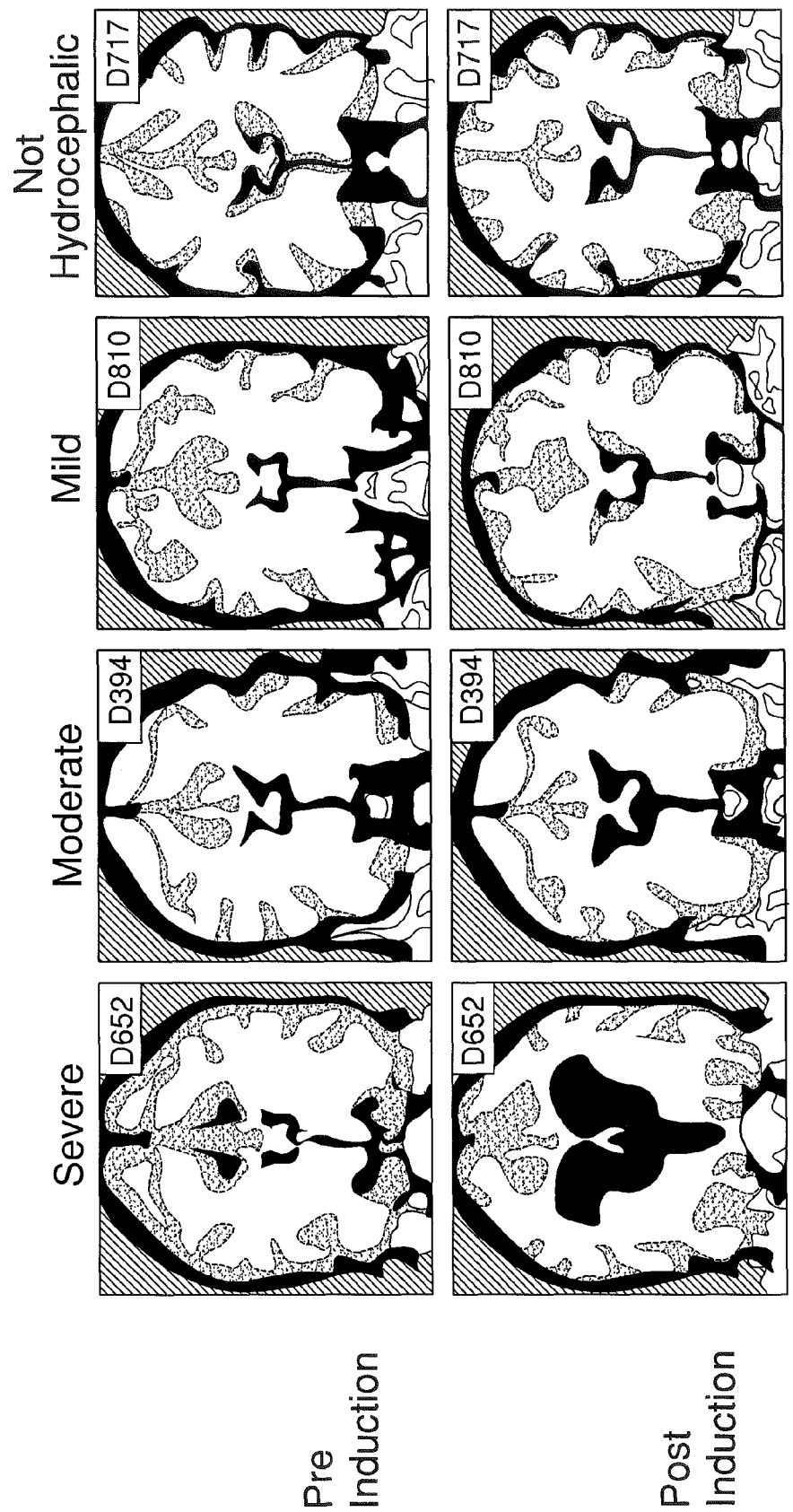
FIG. 21 is a series of magnetic resonance images (MRIs) of the brains of canine having severe, moderate, mild or no hydrocephalus both before and after hydrocephalus induction.

Ventricular size has been the most frequently used parameter in the assessment of hydrocephalus. Ventriculomegaly and induction success was measured via changes in the cerebral ventricular system (lateral, $3^{rd}$, and $4^{th}$ ventricles, foramen of Monro, and cerebral aqueduct) and the brain. MRI were collected before (baseline) and after hydrocephalus induction in order to assess the degree of ventricular enlargement resulting from obstruction (FIG. 21). In the development of the canine model, 81% of the induced animals developed hydrocephalus. Of the 21 hydrocephalus animals successfully induced, 6 animals had mild hydrocephalus, 7 developed moderate hydrocephalus, and 8 developed severe hydrocephalus as determined by Evan's ratio scores. Quantitational 3D volumetric analysis superceded Evan's ratio measures in assessing CH success (FIG. 22A). Using 3D volumetric analysis, estimates of ventricular volume at baseline (range: 0.103-1.908 cc) were compared to post-induction time point (range: 1.019-8.565 cc). In addition, the ratio of ventricle to brain (V:B) was compared between baseline (mean, 7.473×10e-3 cc; range, 9.51×10e-5-1.800×10e-2 cc) and >60 days post-induction (mean, 3.30×10e-2 cc; range, 9.70×10e-3-7.90×10e-2 cc).

Intracranial pressure (ICP) varies with the severity and acuity of hydrocephalus and is often one guide used to determine timing and degree of treatment. During model development, animals were observed to have ICPs within the normal range (mean, 8.73+1.49 mmHg, range, 5.00-13.40 mmHg). Five animals in the initial study had post-operative ICP readings within the "normal range" during a 2-3 week trial with implanted ICP microsensors. By comparison, however, recent data from a small cohort of animals in a study of cerebral blood flow, showed no significant difference in ICP in the animals between baseline and post-CH induction (FIG. 22B). ICP measures have also been useful in calculating intracranial brain compliance (Fukuhara et al., 2001) and CSF turnover.

Acute increases in ICP may result in neurological deficits such as vomiting, anorexia, imbalance, gait ataxia, and decrease awareness of the environment. Routine histology (H+E, CV) of the brain showed intact hemispheric cytoarchitecture and no evidence of general inflammation. Adjacent to the gel obstruction, brainstem and cerebellum cytoarchitecture was normal with some subependymal gliosis in the $4^{th}$ ventricle but little evidence of focal compression. This experimental model of chronic obstructive hydrocephalus was unique in producing a reliable focal obstruction without local compression or general inflammation.

CSF circulation, or the rate of CSF production and the rate of CSF clearance, has recently been made more accurate and reliable with the advancement in ICP monitoring technology. Using modifications of the Masserman and infusion techniques, the rate of response to ICP recovery to CSF infusion and recovery can now be recorded continuously and digitally. The findings showed that the rate of ICP response to CSF infusion and removal could be collected digitally and in real-time using the Multi-Measure Modality device (CMA-Integra Neuroscience, Inc.) recently approved for animal research. Under controlled anesthetic conditions (pH=7.40, $pCO_2$=35.0-45.0 mmHg), CSF production and clearance was obtained intra-operatively using standard CSF removal and infusion techniques. Results demonstrated a decrease in the rate of ICP response after CSF infusion and a significant increase in the rate of ICP response after CSF removal in animals surgically induced with chronic hydrocephalus longer than six weeks.

Figure 23:
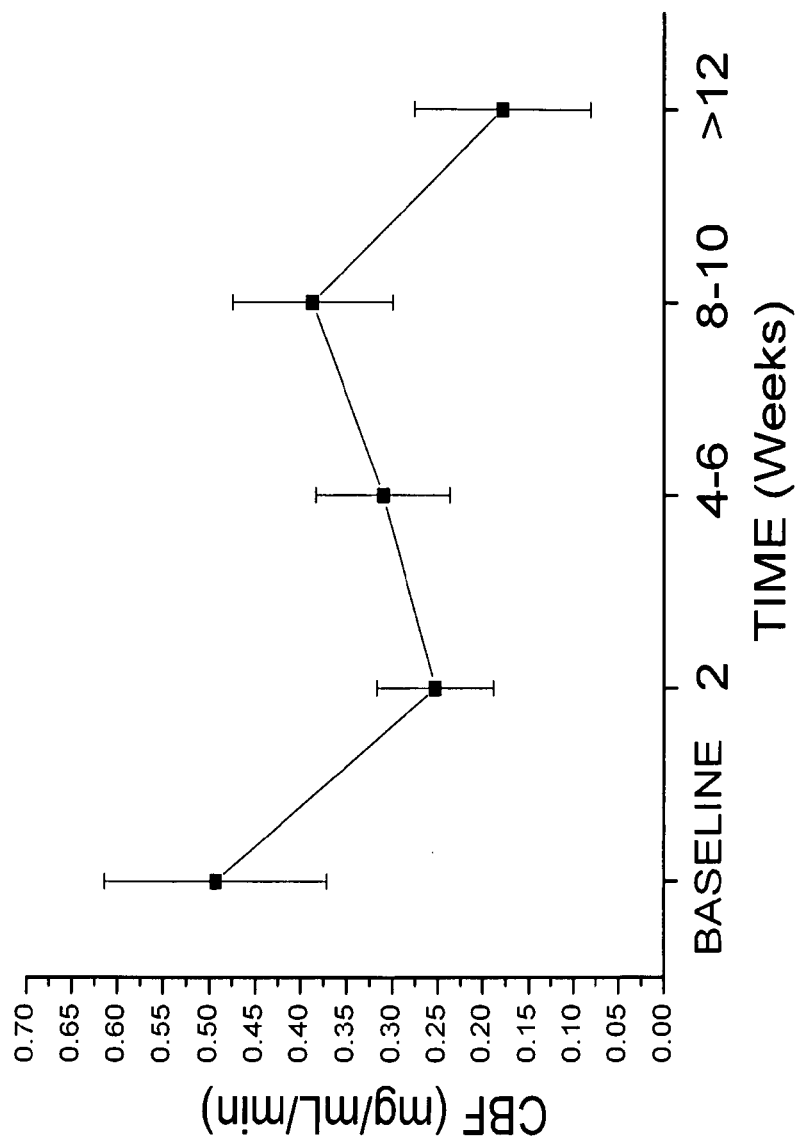
FIG. 23 is a graph illustrating the use of stable isotope labeling to detect and quantify differences in CBF in the experimental model of chronic hydrocephalus over time.

Cerebral Blood Flow (CBF): The microsphere injection method resulted in decreased CBF in the above animal model of CH (see FIG. 23). In brief, there was a 30-40% decrease in CBF immediately following CH induction surgery. After 16 weeks or more, there was a further significant decrease in CBF (40-60%) that might have been related, in part, to decreased cardiac function. These findings were in agreement with clinical findings that patients with CH have deficient CBF. The results are being confirmed using transcranial Doppler techniques.

Intracranial Compliance (ICC): The animal model of CH was employed to investigate ICC across time, and with different ICP conditions (see FIGS. 24A-24B). CH was associated with an immediate and transient increase in ICC followed by decreased ICC in the chronic stage (>12 weeks) of CH. In addition, at normal ICP (5-15 mmHg), ICC was higher in CH than control animals, but at high (15-25 mmHg) ICP and ICC was lower than that in control subjects. The effects of CSF shunt treatment were also investigated. (See Luciano, et al., 2001, *J. Cereb. Blood Flow Metab.* 21(3):285-94 and Fukuhara et al., 2001, J. Neurosurg. 94(4):573-581.)

Figure 25:
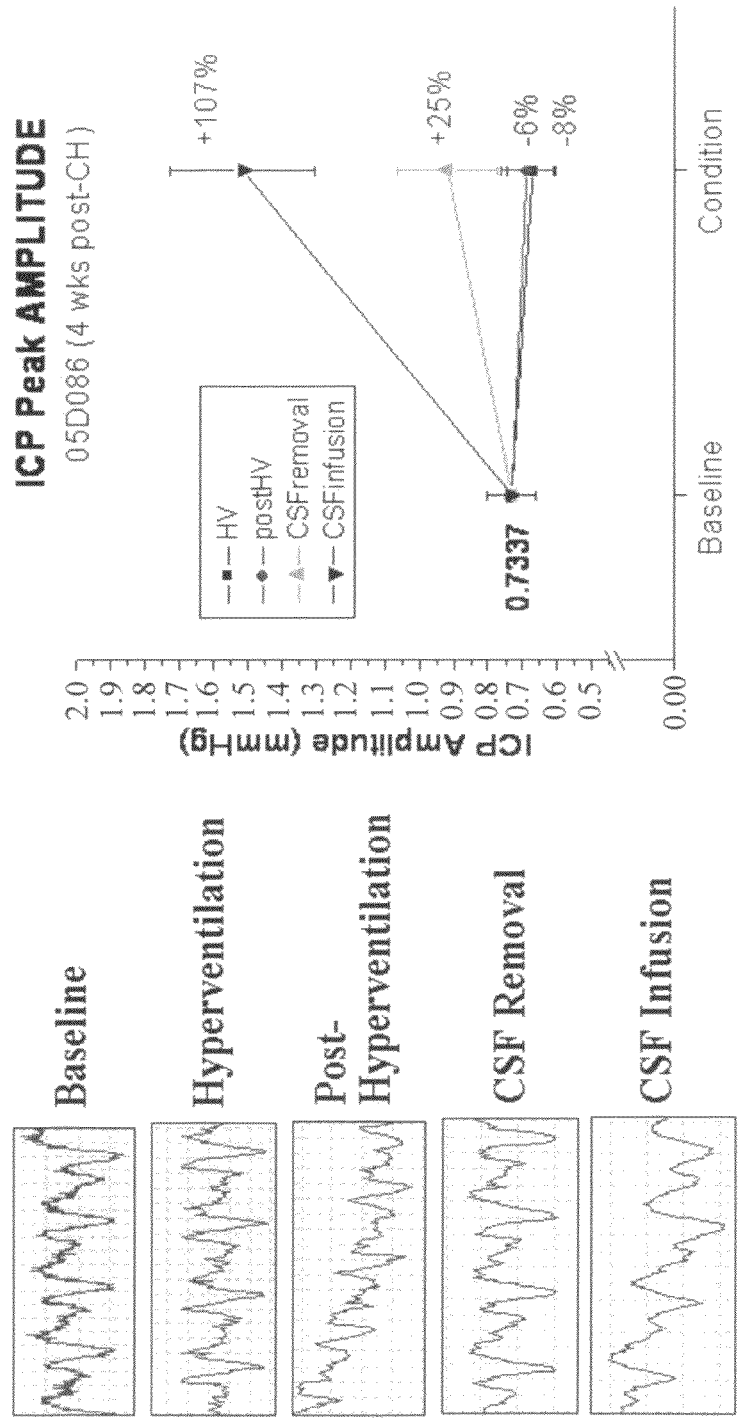
FIG. 25 is a graph illustrating ICP pulse changes in animals with induced chronic hydrocephalus.

Cerebrospinal Fluid Pulsatility (CSFp): There was increased ICPp amplitude after CH induction surgery compared with surgical control animals. In addition, ICPp amplitude showed increased sensitivity to hyperventilation, and CSF removal and infusion compared to baseline (FIG. 25). This data was also used in additional Fourier transform analysis showing differences between CH and control (Congress of Neurological Surgeons, 2005).

Summary of Results

The animal model of obstructive hydrocephalus accurately replicated adult hydrocephalus with gradual ventriculomegaly and ICP, and decreased CBF and abnormal CSF pulsations. The model, unique in its focal non-compressive, non-inflammatory, well-controlled and replicable obstruction, allowed for the study of a more "pure" hydrocephalus and hydrodynamic disorders. Due to animal size, several physiological studies have been performed with relevant clinical implications. This model has been well characterized with regard to changes in volume and pressure, and new measurements for CSF content, turnover, and brain pathology have emerged. Data collected from this model suggested that reduced CBF and CSF hydrodynamics may play a role in the pathophysiology of CH and other neurodegenerative diseases and disorders involving cerebral insufficiency. The effectiveness of an oscillating compliance device in improving CBF and reducing CSF pulsations can be tested experimentally in vivo using the model of chronic hydrocephalus.

Prophetic Example 4

Intraoperative Pulsatility Measures and OCD Procedure

Figure 26:
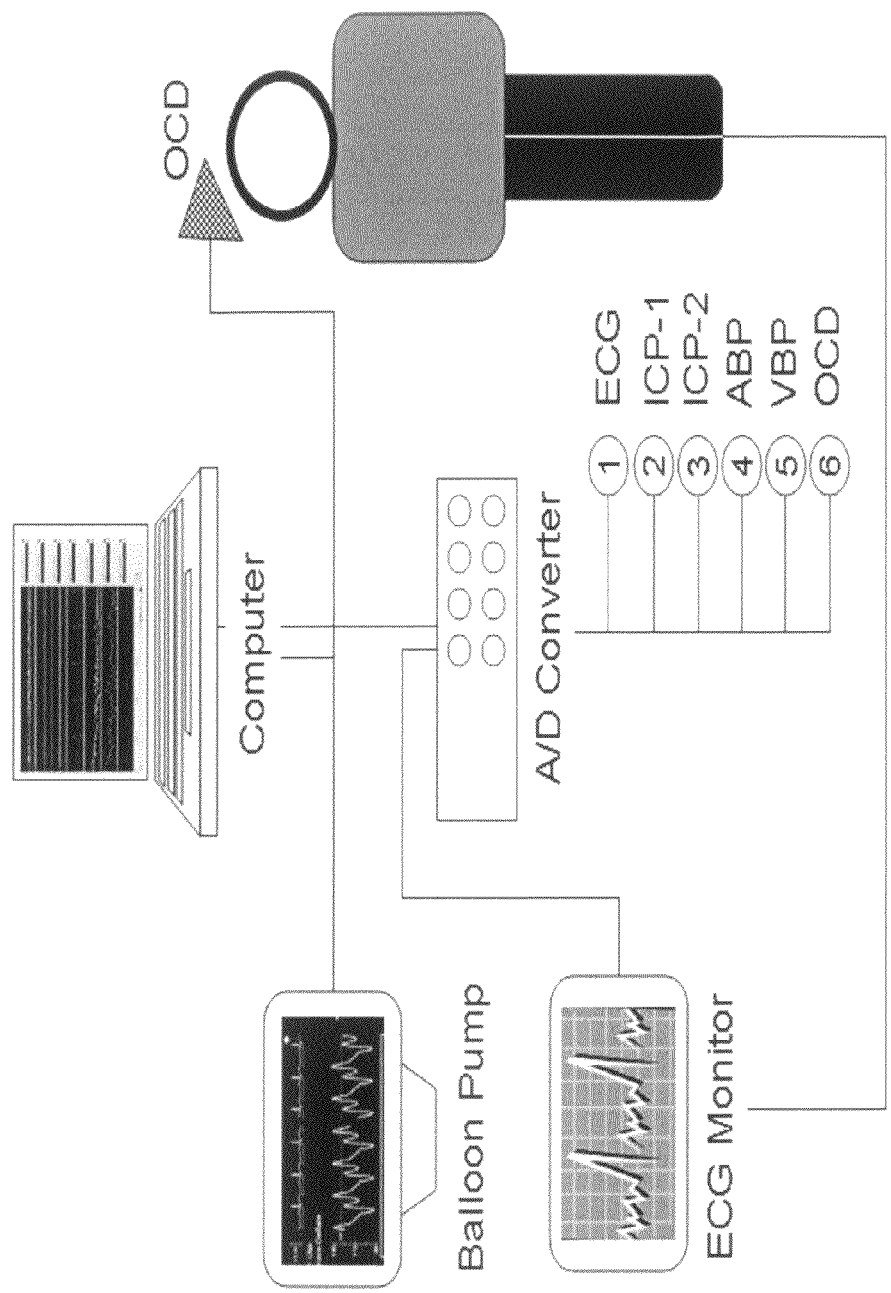
FIG. 26 is a schematic illustrating the intraoperative set up for studies using an oscillating compliance device.

Due to recent evidence indicating the importance of pulse pressure measures in the management of neurosurgical treatments such as hydrocephalus, intracranial (ICP), arterial blood (ABP) and venous blood (VBP) pulsation is recorded. (See intraoperative design in FIG. 26). An on-line/real-time digital capture system (AD Instruments, PowerLab, version 5.2) is used to obtain this information. ICP measures are obtained through standard ICP monitoring (Camino, IntergraNeurosciences), while ABP and VBP are obtained through catheterization (20 gauge angiocatheter) of the internal/common carotid artery and internal/common jugular vein located in the anterior triangle of the neck. ABP and VBP information is coupled to a computer monitor and converted to a digital signal. This minimum-invasive procedure does not subject animals to increases in pain or suffering. This procedure, i.e., ICP, ABP, and VBP pulsatility monitoring, is performed simultaneously while other procedures are being performed, and does not, in any way, affect the study objectives. The information gathered is used in conjunction with and integrated for the purpose of OCD function. The monitoring of ICP, EKG, ABP and VBP is performed intra-operatively under general anesthesia (1-2% Isoflurane). ECG data obtained directly from the subject is transferred through the A/D converter to a computer which is used to control for any required phase delay. Converted data is then be sent to the balloon pump device with the desired information necessary to inflate and deflate the balloon device. All data including ICP, ABP, VBP, raw ECG, modified ECG, and balloon inflation/deflation waveforms are captured digitally and stored. This data is used to optimize the effectiveness of OCD on improving CBF and reducing abnormal ICP pulsations.

Example 5

OCD Prototype and Testing

OCD Prototype Design and Development:

An OCD prototype has been designed for cranial epidural use (FIGS. 27A-B). This OCD balloon, constructed of silicone rubber, was specifically designed for epidural cranial placement (approximately 25 mm diameter, 1 mm thickness) with a volume inflation range of 0.5-5 cc. Due to the fast rate of inflation/deflation and volume of transmission, the OCD balloon catheter was operated with a filled gas (e.g., helium or air) and driven by a pump system developed from commercially available components (see FIGS. 27C-E). The OCD pump system was made up of an: (1) a computer-controlled, arbitrary waveform, reciprocating pump equipped with (2) a stepper motor driven ballscrew linear actuator (Oriental Motors, Inc) attached to a (3) 24 mm diameter, 50 mm stroke anti-stiction air cylinder (Airpot Corp.), (4) ECG cardiotachometer, (5) R-wave discriminator, and (6) digital delay. A computer to control and monitor all pneumonic activation with custom-designed software via RS-232 serial link and serial interface software.

Results of Experimental Studies:

In testing for safety and efficacy, the OCD should demonstrate:

1. Safe placement and tolerance of the implanted oscillating balloon device.
2. Modulation, especially diminution, of the ICP curve with cardiac synchronized balloon volume change.
3. Reversibility of ICP effect based on synchronous operation of the balloon.
4. Increased cerebral blood flow with synchronous balloon operation.
5. Reversible cerebral blood flow changes based on balloon operation and on ICP curve effect.
6. Increased and reversible oxygen delivery with synchronous balloon operation.

The OCD was successfully employed in three experimental animals (canines) and its effectiveness on blood flow, oxygen delivery, and pulsatility evaluated. Quantitative methods to measure blood flow, pressure and velocity via commercially available blood flow (Transonic Systems Inc., model #3PBS; Itheca, N.Y. USA) and pressure probes (Volcano, Combo Wire XT, Rancho Cordova, Calif., USA), oxygen probes (Integra LICOX System, Model #CC1-SB; Plainsboro, N.J. USA), Transcranial Doppler (TCD), and microsphere blood flow technique (BioPhysics Assay Laboratory, Inc.; #A-OMS01; Worchester, Mass. USA) were used. OCD effectiveness was demonstrated in normal animals as well as in an animal model of chronic hydrocephalus (see Example 3), that was shown to have reduced CBF and oxygen, and altered intracranial compliance (Johnson M J et al., *J. Neurosci Methods* 91:55-65, 1999; Fukuhara et al., 2001, J Neurosurg. 94(4):573-581; Dombrowski S M et al., *J. Cereb Blood Flow Metab*, 2006).

Use of the cranial-epidural OCD showed the following:

(1) OCD balloon could be successfully implanted via right frontal-parietal (~3 cm$^2$) craniotomy and activated with little or no physiologically adverse effects on the animal (i.e., heart rate, arterial blood pressure, arterial blood gas, etc.).

(2) ICP pulse amplitude can be reduced approximately 70%, which was reversible with the system off (FIG. 28).

(3) CBF velocity, obtained via TCD in left/right (L/R) Siphon (corresponding to internal carotid artery) and Basilar artery, increased with OCD activation (FIG. 29), and was reversible with non-activation; effects of increased CBF velocity greater on ipsilateral (same side as implanted balloon device) versus contralateral (opposite side of implanted balloon device) hemisphere.

(4) Oxygen saturation to the prefrontal cortex was improved during OCD activation by ~40% in an experimental animal of chronic hydrocephalus suggesting a physiologically significant increase in oxygen delivery.
(5) Extended OCD implantation in vivo well-tolerated for 80 days.

Prophetic Example 6

Additional OCD Testing and Components

The OCD can be further tested for an ability to demonstrate:
1. Increased cerebral blood flow in addition to increased blood velocity.
2. Association of increased flow with both pump operation and with flattened ICP wave.
3. Flow and oxygen effect reversibility (i.e., dependence on synchronous balloon operation).
4. Estimation of magnitude and distribution of flow and oxygen effect to establish physiological significance.
5. Reliability of effect and independence from other confounding factors (such as $CO_2$, temperature, level of anesthesia).

Additional studies require more animals (minimally 2-3 and preferably 8 animals) to focus on establishing a positive and reversible effect of the OCD and indications of significance (spatial, temporal and physiological), reliability and independence of other factors impacting cerebral blood flow. After a positive and reversible effect is demonstrated, depending on the consistency and quality of the findings, studies can then be replicated with additional animals to insure reproducibility and include further variations in balloon function and physiological measurement to better establish and characterize efficacy.

Other desirable components of an OCD or OCD system would include:
1. A "user friendly" pump interface to facilitate more efficient "on the fly" balloon function modulation for each experiment. This allows for a more empirical experimentation for each preparation and more data.
2. Blood flow probes that allow for real time evaluation of blood flow.
3. Flow imaging (e.g., SPECT) devices to allow for regional evaluation of blood flow changes.
4. Expanded area ICP wave monitoring modulation and/or more ICP sensors to evaluate the degree of global impact on compliance and determine optimum positioning of device.

While this invention has been particularly shown and described with references to preferred embodiments thereof, it will be understood by those skilled in the art that various changes in form and details may be made therein without departing from the scope of the invention encompassed by the appended claims.

What is claimed is:

1. An oscillating compliance device comprising a compressible composition capable of being placed within an epidural space or a cerebrospinal fluid (CSF) space of an individual's brain or spinal cord, wherein the compressible composition is capable of free expansion and compression to affect the individual's intracranial compliance (ICC), cerebral blood flow (CBF), intracranial pressure (ICP) pulsatility, or combinations thereof, a pump coupled to said compressible composition for the expansion and compression of the compressible composition and a reservoir coupled to said pump, a biorhythm sync connected to said pump and for connecting to a source of the individual's biorhythm for capturing an associated biorhythm waveform in order to synchronize said pump with the individual's biorhythm source, and configured for displacing a substance from the compressible composition and returning the substance to the compressible composition, the compressible composition comprising a generally planar balloon being about 5-50 mm long and configured to be between less than about 1 mm, to 5 mm thick when deflated and inflated, the pump being reciprocating and comprising a linear stroke fluid cylinder attached to and mechanically driven by a ball screw linear actuator that is driven by a stepper motor, the biorhythm sync providing a repeating cadence waveform having a peak that is capable of repeating under a second of time, for selectively synchronizing with desired phases of the biorhythm waveform, the cadence waveform having a predetermined shape, and necessary data for controlling the pump's expansion and compression, the pump's expansion and compression of the compressible composition being adjustably selected by the cadence waveform for altering ICP pulsatility waveforms, including increasing and decreasing ICP pulsatility amplitude as desired.

2. The oscillating compliance device of claim 1 wherein the compressible composition is a balloon catheter comprising a substance selected from the group consisting of: a fluid and a malleable substance.

3. The oscillating compliance device of claim 1 wherein the reservoir is configured to be placed in a location selected from the group consisting of: an extra-craniospinal space, a subcutaneous space and within a body cavity.

4. The oscillating compliance device of claim 1 wherein the reservoir is configured to be placed within a body cavity selected from the group consisting of: the pericardial sac and the peritoneal sac.

5. An oscillating compliance system comprising two or more oscillating compliance devices of claim 1.

6. The oscillating compliance system of claim 5 wherein the compressible composition of each of the two or more oscillating compliance devices is a balloon catheter comprising a substance selected from the group consisting of: a fluid and a malleable substance.

7. The oscillating compliance device of claim 5 wherein the reservoir of the two or more oscillating compliance devices is configured to be placed in a location selected from the group consisting of: extra-craniospinal, subcutaneous and within a body cavity.

8. An oscillating compliance device comprising:
a compressible composition capable of being placed within an epidural space or a cerebrospinal fluid (CSF) space of a patient's brain or spinal cord;
a pump coupled to said compressible composition for the expansion and compression of the compressible composition;
a reservoir coupled to said pump; and
a biorhythm sync connected to said pump and for connecting to a source of the patient's biorhythm for capturing an associated biorhythm waveform in order to synchronize said pump with the patient's biorhythm source, and configured for displacing a substance from the compressible composition and returning the substance to the compressible composition, the compressible composition comprising a generally planar balloon being about 5-50 mm long and configured to be between less than about 1 mm, to 5 mm thick when deflated and inflated, the pump being reciprocating and comprising a linear stroke fluid cylinder attached to and mechanically driven by a ball screw linear actuator that is driven by a stepper motor, the biorhythm sync providing a repeating cadence waveform having a peak that is capable of repeating under a second of time, for selectively synchronizing with desired phases of the biorhythm waveform, the cadence waveform having a predetermined shape, and necessary data for controlling the pump's expansion and compression, the pump's expansion and compression of the compressible composition being adjustably selected by the cadence waveform for altering ICP pulsatility waveforms, including increasing and decreasing ICP pulsatility amplitude as desired.

9. The oscillating compliance device of claim 8 wherein the compressible composition is a balloon catheter comprising a substance selected from the group consisting of: a fluid and a malleable substance.

10. The oscillating compliance device of claim 8 wherein the reservoir is configured to be placed in a location selected from the group consisting of: extra-craniospinal, subcutaneous and within a body cavity.

11. The oscillating compliance device of claim 8 wherein the reservoir is configured to be placed within a body cavity selected from the group consisting of the pericardial sac or the peritoneal sac.

12. The oscillating compliance device of claim 8 wherein the source of the patient's biorhythm is from the group consisting of: an electrical rhythm of the patient's heart, a cardiovascular pressure pulse of the patient and an ICP wave of the patient.

13. The oscillating compliance device of claim 12 wherein the biorhythm source is an electrical rhythm of the patient's heart and the biorhythm sync is a cardiac sync.

14. An oscillating compliance device comprising:
a compressible composition capable of being placed within an epidural space or a cerebrospinal fluid (CSF) space of a patient's brain or spinal cord;
a tube coupled to said compressible composition;
a reservoir configured to be placed in the patient's pericardial space coupled to said tube, wherein said reservoir is capable of free expansion and compression due to contraction and expansion of the patient's heart;
a pump coupled to the reservoir and the compressible composition for the expansion and compression of the compressible composition to affect the patient's ICC, CBF, ICP pulsatility or combinations thereof; and
a biorhythm sync connected to said pump and for connecting to a source of the patient's biorhythm for capturing an associated biorhythm waveform in order to synchronize said pump with the patient's biorhythm source, and configured for displacing a substance from the compressible composition and returning the substance to the compressible composition, the compressible composition comprising a generally planar balloon being about 5-50 mm long and configured to be between less than about 1 mm, to 5 mm thick when deflated and inflated, the pump being reciprocating and comprising a linear stroke fluid cylinder attached to and mechanically driven by a ball screw linear actuator that is driven by a stepper motor, the biorhythm sync providing a repeating cadence waveform having a peak that is capable of repeating under a second of time, for selectively synchronizing with desired phases of the biorhythm waveform, the cadence waveform having a predetermined shape, and necessary data for controlling the pump's expansion and compression, the pump's expansion and compression of the compressible composition being adjustably selected by the cadence waveform for altering ICP pulsatility waveforms, including increasing and decreasing ICP pulsatility amplitude as desired.

15. The oscillating compliance device of claim 14 wherein the tube allows free exchange between the compressible composition and the reservoir.

16. The oscillating compliance device of claim 15 wherein the compressible composition is a balloon catheter comprising a substance selected from the group consisting of: a fluid and a malleable substance.

17. A method for protecting an individual's brain from arterial pulsations entering the individual's cranial cavity comprising:
displacing a substance from a compressible composition in the individual's intracranial or intraspinal space during systole using one or more oscillating compliance devices of claim 1; and
returning the substance to the compressible composition in the individual's intracranial or intraspinal space during diastole using said one or more oscillating compliance devices,
wherein the compressible composition is capable of expansion and compression.

18. One or more oscillating compliance devices which, when in use, protects an individual's brain from arterial pulsations entering the individual's cranial cavity, wherein the one or more oscillating compliance devices comprise a compressible composition capable of being placed within an epidural space or a cerebrospinal fluid (CSF) space of the individual's brain or spinal cord, a pump coupled to said compressible composition for the expansion and compression of the compressible composition, a reservoir coupled to said pump and a biorhythm sync connected to said pump for connecting to a source of the individual's biorhythm for capturing an associated biorhythm waveform for synchronization of said pump with said biorhythm, and configured for displacing a substance from the compressible composition and returning the substance to the compressible composition, the compressible composition comprising a generally planar balloon being about 5-50 mm long and configured to be between less than about 1 mm, to 5 mm thick when deflated and inflated, the pump being reciprocating and comprising a linear stroke fluid cylinder attached to and mechanically driven by a ball screw linear actuator that is driven by a stepper motor, the biorhythm sync providing a repeating cadence waveform having a peak that is capable of repeating under a second of time, for selectively synchronizing with desired phases of the biorhythm waveform, the cadence waveform having a predetermined shape, and necessary data for controlling the pump's expansion and compression, the pump's expansion and compression of the compressible composition being adjustably selected by the cadence waveform for altering ICP pulsatility waveforms, including increasing and decreasing ICP pulsatility amplitude as desired.

19. An oscillating compliance device comprising:
a compressible composition capable of being placed within an epidural or CSF space of the patient's brain or spinal cord;
a pump coupled to said compressible composition for the expansion and compression of the compressible composition;
a reservoir coupled to said pump; and
a biorhythm sync connected to said pump and for connecting to a source of a patient's biorhythm in order to synchronize said pump with the patient's biorhythm source for capturing an associated biorhythm waveform, and configured for displacing a substance from the compressible composition and returning the substance to the compressible composition, the compressible composition comprising a generally planar balloon being about 5-50 mm long and configured to be between less than about 1 mm, to 5 mm thick when deflated and inflated, the pump being reciprocating and comprising a linear stroke fluid cylinder attached to and mechanically driven by a ball screw linear actuator that is driven by a stepper motor, the biorhythm sync providing a repeating cadence waveform having a peak that is capable of repeating under a second of time, for selectively synchronizing with desired phases of the biorhythm waveform, the cadence waveform having a predetermined shape, and necessary data for controlling the pump's expansion and compression, the pump's expansion and compression of the compressible composition adjustably selected by the cadence waveform for altering ICP pulsatility waveforms, including increasing and decreasing ICP pulsatility amplitude as desired.

20. A method of altering intracranial pressure (ICP) pulsatility in an individual comprising:

in synchrony with a biorhythm of the individual, with an open catheter, displacing about 0.5 to 25 cc of a fluid from the individual's intracranial or intraspinal space using one or more oscillating compliance devices; and returning the fluid with the open catheter to the individual's intracranial or intraspinal space using said one or more oscillating compliance devices, the fluid being displaced to and from a reservoir with a pump, said pump being connected to and controlled by a biorhythm sync that is connected to a biorhythm source for capturing an associated biorhythm waveform of the individual for synchronizing said pump with the biorhythm source, and configured for displacing the fluid from the individual's intracranial or intraspinal space and returning the fluid to the individual's intracranial or intraspinal space, the pump being reciprocating and comprising a linear stroke fluid cylinder attached to and mechanically driven by a ball screw linear actuator that is driven by a stepper motor, the biorhythm sync providing a repeating cadence waveform having a peak that is capable of repeating under a second of time, for selectively synchronizing with desired phases of the biorhythm waveform, the cadence waveform having a predetermined shape, and necessary data for controlling the pump's expansion and compression, the pump's expansion and compression being adjustably selected by the cadence waveform for altering ICP pulsatility waveforms, including increasing and decreasing ICP pulsatility amplitude as desired.

21. The method of claim 20 further comprising displacing and returning the fluid in synchrony with a cardiac rhythm.

22. The method of claim 20 further comprising treating conditions of a brain disorder.

23. A device for flow altering intracranial pressure (ICP) pulsatility of an individual comprising:

an open catheter capable of being placed within an epidural or CSF space of the individuals brain or spinal cord;

a pump coupled to the catheter for displacing and returning about 0.5 to 25 cc of a fluid to and from the individual's intracranial or intraspinal space with the open catheter;

a reservoir coupled to the pump; and a biorhythm sync connected to the pump and for connecting to a biorhythm source for capturing an associated biorhythm waveform of the individual in order to synchronize the pump with the biorhythm source, and configured for displacing the fluid from the individual's intracranial or intraspinal space and returning the fluid to the individual's intracranial or intraspinal space, the pump being reciprocating and comprising a linear stroke fluid cylinder attached to and mechanically driven by a ball screw linear actuator that is driven by a stepper motor, the biorhythm sync providing a repeating cadence waveform having a peak that is capable of repeating under a second of time, for selectively synchronizing with desired phases of the biorhythm waveform, the cadence waveform having a predetermined shape, and necessary data for controlling the pump's expansion and compression, the pump's expansion and compression being adjustably selected by the cadence waveform for altering ICP pulsatility waveforms, including increasing and decreasing ICP pulsatility amplitude as desired.

24. The device of claim 23 in which the biorhythm source is a cardiac rhythm.

* * * * *